United States Patent
Phillips et al.

(10) Patent No.: US 7,022,524 B1
(45) Date of Patent: Apr. 4, 2006

(54) INCREASING PLANT GROWTH WITH LUMINOL

(75) Inventors: Donald A. Phillips, Davis, CA (US); Cecillia M. Joseph, Davis, CA (US); James R. Sanborn, Sacramento, CA (US)

(73) Assignee: The Regents of the University of California, Office of Technology Transfer, Oakland, CA (US)

( * ) Notice: Subject to any disclaimer, the term of this patent is extended or adjusted under 35 U.S.C. 154(b) by 0 days.

(21) Appl. No.: 09/831,958

(22) PCT Filed: Nov. 17, 1999

(86) PCT No.: PCT/US99/27318

§ 371 (c)(1),
(2), (4) Date: Oct. 15, 2001

(87) PCT Pub. No.: WO00/29607

PCT Pub. Date: May 25, 2000

Related U.S. Application Data

(63) Continuation-in-part of application No. 09/369,955, filed on Aug. 6, 1999, now abandoned, which is a continuation-in-part of application No. 09/193,801, filed on Nov. 17, 1998, now Pat. No. 6,365,406, and a continuation-in-part of application No. 09/193,600, filed on Nov. 17, 1998, now abandoned.

(51) Int. Cl.
*A01N 43/60* (2006.01)

(52) U.S. Cl. .................... 435/420; 504/116.1; 504/235; 504/353; 47/58.1

(58) Field of Classification Search ................ 435/420; 504/235, 116.1, 353; 47/58.1
See application file for complete search history.

(56) References Cited

U.S. PATENT DOCUMENTS

| | | | |
|---|---|---|---|
| 4,436,547 A | | 3/1984 | Sampson et al. |
| 4,704,161 A | | 11/1987 | White et al. |
| 4,789,436 A | | 12/1988 | Greenbaum |
| 4,849,008 A | * | 7/1989 | Schroth et al. ............ 504/117 |
| 5,045,461 A | * | 9/1991 | Scott ............................ 71/7 |
| 5,106,648 A | * | 4/1992 | Williams ..................... 427/4 |
| 5,116,406 A | | 5/1992 | Hyeon |
| 5,298,483 A | | 3/1994 | Yokoyama et al. |
| 5,403,583 A | | 4/1995 | Liu et al. |
| 5,415,672 A | | 5/1995 | Fahey et al. |
| 5,432,079 A | * | 7/1995 | Johansen et al. ............ 435/6 |
| 5,597,400 A | | 1/1997 | Nonomura et al. |
| 5,797,976 A | | 8/1998 | Yamashita |
| 5,919,448 A | | 7/1999 | Maekawa et al. |
| 5,925,538 A | | 7/1999 | Perkins et al. |
| 5,932,701 A | | 8/1999 | Black et al. |
| 5,935,571 A | | 8/1999 | Aino et al. |
| 5,958,104 A | * | 9/1999 | Nonomura et al. |

FOREIGN PATENT DOCUMENTS

| | | |
|---|---|---|
| JP | 60115501 | 6/1985 |
| JP | 01086822 | 3/1989 |
| JP | 03109304 | 5/1991 |
| JP | 04166017 | 6/1992 |
| JP | 08143406 | 11/1994 |
| WO | WO 96/21737 A1 | 7/1996 |
| WO | WO 97/01572 A1 | 1/1997 |

OTHER PUBLICATIONS

Barea et al., "Impact on Arbuscular Mycorrhiza Formation of *Pseudomonas* Strains Used as Inoculants for Biocontrol of Soil–Borne Fungal Plant Pathogens"; *Applied and Environmental Microbiology*, 64(6):2304–2307 (1998).

Boadbent et al., "C–Acetylphloroglucinols From *Pseudomonas Fluorescens*"; *Phytochemistry*, 15:1785 (1976).

Brimecombe et al., "Effect of genetically modified *Pseudomonas fluorescens* strains on the uptake of nitrogen by pea from $^{15}N$ enriched organic residues"; *Letters in Applied Microbiology*, 26:155–160 (1998).

Brown, M.E., "Plant Growth Substances Produced by Micro–organisms of Soil and Rhizosphere"; *J. Appl. Bact.*, 35:443–451 (1972).

Coquard et al., "Molecular cloning and characterisation of the ribC gene from *Bacillus subtilis*: a point mutation in ribC results in riboflavin overproduction"; *Mol. Gen. Genet.*, 254:81–84 (1997).

Deckert, Gerard et al., "The complete genome of the hyperthermophilic bacterium *Aquifex aeolicus*"; *Nature*, 392:353–358 (Mar. 1998).

DeJong, Ted M. et al., "Nitrogen Stress and Apparent Photosynthesis in Symbiotically Grown *Pisum sativum L.*"; *Plant Physiol*, 68:309–313 (1981).

Eberhardt et al., "Cloning, sequencing, mapping, and hyperexpression of the ribC gene coding for riboflavin synthase of *Escherichia coli*"; *Eur. J. Biochem.*, 242:712–719 (1996).

(Continued)

*Primary Examiner*—Leon B. Lankford, Jr
(74) *Attorney, Agent, or Firm*—Townsend and Townsend and Crew LLP

(57) ABSTRACT

The present invention provides novel enhancers of photosynthesis and plant growth and methods of using same. In one embodiment, the enhancer is derived from a microorganism. In alternative embodiments, the compounds are microbial extracts, microbial secretion products, and microbially generated natural products. The invention also provides a method for increasing net photosynthesis in a plant by applying an agent comprising triacetylphloroglucinol, diacetylphloroglucinol or monoacetylphloroglucinol to the plant in an amount effective in increasing net photosynthesis in the plant. The invention further provides novel bacterial genes and recombinant microorganisms comprising these genes which are used to practice the methods of the invention.

9 Claims, No Drawings

OTHER PUBLICATIONS

Fenton et al., "Exploitation of Gene(s) Involved in 2,4–Diacetylphloroglucinol Biosynthesis to Confer a New Biocontrol Capability to a *Pseudomonas* Strain"; *Applied and Environmental Biology*, 58(12):3873–3878 (Dec. 1992).

Fleischmann et al., "Whole–Genome Random Sequencing and Assembly of *Haemophilus influenzae* Rd"; *Science*, 269:496–498 (Jul. 1995).

Gendy et al., "The response of growth, nodulation, and yield of soybean plants treated with riboflavin and nicotinic acid"; *Beitr.trop.Landwirtsch.Vet.med.*, 30 H.3:271–281 (1992).

Grant, R. and Grant, C. Eds., *Grant & Hackh's Chemical Dictionary*, Fifth Edition (1987).

Grochowska, "Chromatographic Degradation of Phloridzin"; *Plant Physiol.*, 41:432–436 (1966).

Hansen, G. K., *Physiol. Plant*, 39(4):275–279 (1977).

Jones, O.P., "Effect of phloridzin and phloroglucinol on apple shoots"; *Nature*, 262:592 (Jul. 1976).

Kaneko et al., "Sequence Analysis of the Genome of the Unicellular Cyanobacterium *Synechocystis* sp. Strain PCC6803. II. Sequence Determination of the Entire Genome and Assignment of Potential Protein–coding Regions"; *DNA Reasearch*, 3:109–136 (1996).

Keel et al., "Pseudomonads as Antagonists of Plant Pathogens in the Rhizosphere: Role of the Antibiotic 2,4–Diacetylphloroglucinol in the Suppression of Black Root Rot of Tobacco"; *Symbiosis*, 9:327–341 (1990).

Lapidus et al., "Sequencing and functional annotation of the *Bacillus subtilis* genes in the 200 kb mB–dnaB region"; *Microbiology*, 143:3431–3441 (1997).

Lee et al, "The *Lux* Genes in *Photobacterium Leiognathi* are Closely Linked With Genes Corresponding in Sequence to Riboflavin Synthesis Genes"; 186(2): 690–697 (1992).

Lee et al., "Riboflavin Synthesis Genes Are Linked with the *lux* Operon of *Photobacterium phosphoreum*"; *Journal of Bacteriology*, 176(7):2100–2104 (Apr. 1994).

Lugtenberg et al., "Microbial stimulation of plant growth and protection from disease"; *Current Opinion in Biotechnology*, 2:457–464 (1991).

Marré et al., "Azione Di Stimolo Della Florizina Sulla Fotosintesi E Sulla Fotolisi Da Parte Di Cloroplasti Isolati"; *Nuovo Giomale Botanico Italiano*, LXII:566, (1955).

Naseby et al., "Impact of wild–type and genetically modified *Pseudomonas fluorescens* on soil enzyme activities and microbial population structure in the rhizosphere of pea"; *Molecular Ecology*, 7:617–625 (1998).

Nelson et al., "Evidence for lateral gene transfer between Archaea and Bacteria from genome sequence of *Thermotoga Maritima*"; *Nature*, 399:323–329 (May 1999).

Oertli, J.J., "Exogenous application of vitamins as regulators for growth and development of plants—a review"; *Z. Pflanzenemahr. Bodenk.*, 150:375–391 (1987).

Raaijmakers et al., "Natural Plant Protection by 2,4–Diacetylphloroglucinol–Producing *Pseudomonas* spp. in Take–All Decline Soils"; *Molecular Plant–Microbe Interactions*, 11(2):144–152 (1998).

Rao et al., "Reversal of Chloramphenicol Inhibited Growth By Riboflavin in Green Gram (*Phaseolus Radiatus* L.)"; *Current Science*, 44(11):399–400 (Jun. 1975).

Rao et al., "$^{14}$C Incorporation in Chloramphenicol Inhibited Growth And Its Reversal By Riboflavin in Green Gram"; *Current Science*, 44(22):818 (1975).

Rao, P. Gopala, "Influence of Riboflavin on Growth, Respiration, and Chlorophyll and Protein Contents in Green Gram (*Phaseolus Radiatus Linn.*)"; *Current Science*, 42(16):580–581 (Aug. 1973).

Ryle et al., "The Respiratory Costs of Nitrogen Fixation in Soyabean, Cowpea, and White Clover"; *Journal of Experimental Botany*, 30(114):145–153 (Feb. 1979).

Schott et al., "Riboflavin Synthases of *Bacillus subtilis*"; *The Journal of Biological Chemistry*, 265(8):4204–4209 (Mar. 1990).

Shanahan et al., "Isolation, trace enrichment and liquid chromatographic analysis of diacetylphloroglucinol in culture and soil samples using UV and amperometric detection"; *Journal of Chromatography*, 606:171–177 (1992).

Shanahan et al., "Liquid chromatographic assay of microbially derived phloroglucinol antibiotics for establishing the biosynthetic route to production, and the factors affecting their regulation"; *Analytica Chimica Acta*, 272:271–277 (1993).

Song et al., "Purification of Phytochrome by Affi–Gel Blue Chromatography, an Effect of Lumichrome on Purified Phytochrome"; *Analytical Biochemistry*, 117:32–39 (1981).

Streit et al., "Biotin and Other Water–Soluble Vitamins Are Key Growth Factors for Alfalfa Root Colonization by *Rhizobium meliloti* 1021"; *Molecular Plant–Microbeinteractions*, 9(5):330–338 (1996).

Strzelczyk et al., "Synthesis of Auxins from Tryptophan and Tryptophan–precursors by Fungi Isolated from Mycorrhizae of Pine (*Pinus silvestris* L.)"; *ACTA Microbiologica Polonica*, 26(3):255–264 (1977).

Taura et al., "Insertional disruption of the nusB (ssyB) gene leads to cold–sensitive growth of *Escherichia coli* and suppression of the secY24 mutation"; *Mol. Gen. Genet.*, 234:429–432 (1992).

Volpin et al., "Respiratory Elicitors from *Rhizobium meliloti* Affect Intact Alfalfa Roots"; *Plant Physiol.*, 116:777–783 (1998).

West et al., "Synthesis of Growth Factors by *Rhizobium trifolil*"; *Nature*, No. 3591, pp. 397–398 (Aug. 1938).

Yanagita et al., "A Bacterial Riboflavin Hydrolase"; *The Journal of Biological Chemistry*, 221(2): 593–607 (Aug. 1956).

Zhang et al., "Phosphoenolpyruvate Carboxylase Protein Kinase from Soybean Root Nodules: Partial Purification, Characterization, and Up/Down–Regulation by Photosynthate Supply from the Shoots"; *Archives of Biochemistry and Biophysics*, 343(2):260–268 (Jul. 1997).

\* cited by examiner

INCREASING PLANT GROWTH WITH LUMINOL

CROSS-REFERENCES TO RELATED APPLICATIONS

The present application is a 371 of PCT/US99/27318 filed Nov. 17, 1999 which is a continuation-in-part application ("CIP" of U.S. patent application Ser. No. 09/369,955, filed Aug. 6, 1999, now abandoned, which is a CIP of U.S. Ser. No. 09/193,801, filed Nov. 17, 1998 now U.S. Pat. No. 6,365,406 and U.S. Ser. No. 09/193,600, filed Nov. 17, 1998 now abandoned. The aforementioned applications are explicitly incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with Government support under Grant No. IBN-9722988, awarded by the United States National Science Foundation. The Government may have certain rights in this invention.

FIELD OF THE INVENTION

The present invention relates generally to plant science. In particular, it relates to novel methods of enhancing net photosynthesis and to plant growth and novel compositions and bacteria genes useftil in these methods.

BACKGROUND OF THE INVENTION

The present invention provides novel enhancers of net photosynthesis and methods of enhancing net photosynthesis and plant growth. Due to the ever increasing need to grow crops more efficiently, the ability to increase a plant's growth rate would be of great social and economic value. An attractive biochemical target to accomplish this is the plant's ability to fix carbon dioxide by photosynthesis. The ability to enhance net photosynthesis will allow the grower to generate a plant that is faster growing and/or has increased biomass in, for example, storage products, such as starch (polysaccharides), protein or fats.

Researchers have been investigating means to boost a plant's photosynthetic rate in a variety of ways. Some examples include exposing a plant to light with the same wavelengths as sunlight (see, e.g., JP04166017); generating transgenic plants with exogenous genes involved in photosynthesis (see, e.g., WO 96/21737); application of various chemicals to increase the rate of photosynthesis (see, e.g., JP03109304, U.S. Pat. Nos. 4,704,161 and 5,597,400); and applying chemicals to suppress photorespiration, resulting in an increase in the efficiency of photosynthesis (see, e.g., JP01086822, JP60115501, JP55136205, JP55036437).

However, prior to this invention, no enhancers of net photosynthesis have been identified. Furthermore, the present invention taps a rich, yet to date untapped source, of enhancers of net photosynthesis from microorganisms, particularly bacteria. Identification of enhancers of net photosynthesis and plant growth from microorganisms would offer many benefits. For example, the reagent, as a natural product, can be generated on a large, industrial scale using conventional techniques. This eliminates the need to structurally analyze and/or synthetically produce the bioactive component of the microbial extract. Furthermore, if the microorganism can grow in soil or can colonize plant roots, application of the microbe to the soil could be equivalent to applying the bacterial natural product or extract itself. If the genetic mechanism responsible for producing the bioactive agent is found, transgenic microorganisms can be constructed. Thus, any soil-borne or plant (e.g., root, shoot, leaf)-colonizing microorganism can be recombinantly manipulated to generate an enhancer of net photosynthesis or enhancer of plant growth.

Taxonomic labels on the most frequently used rhizobia have been in a state of flux for the past decade, but the two most important species currently are known as *Sinorhizobium meliloti* for alfalfa and *Bradyrhizobium japonicum* for soybean (Phillips and Martinez-Romero, 2000, Biological nitrogen fixation. In: Encyclopedia of Microbiology, $2^{nd}$ edition, ed. J. Lederberg. Academic Press, San Diego. Vol 1: In press.) A less studied species, *Sinorhizobium fredii*, formerly called *Rhizobium fredii*, forms root nodules on both alfalfa and soybean (Hashem et al, 1997, Symbiosis 22:255–264) and thus may have outstanding commercial potential for future inoculants.

Genetic attempts to improve the competitiveness and commercial performance of rhizobia have centered on a small number of traits, including enhancement of $N_2$-fixation capacity (Bosworth et al, 1994, Appl. Environ. Microbiol. 60:3815–3832), production of antibiotics that impair competing bacteria (Kent et al, 1998, Appl. Environ. Microbiol. 64:1657–1662), and the use of $H_2$ as an energy source (Kent et al, 1998, Appl. Environ. Microbiol. 64:1657–1662). Other plant-associated bacteria are claimed to promote plant growth by supplying plant hormones, rather than by reducing $N_2$ to ammonia. *Azospirillum*, one genus representative of this group, has been used successfully as an agricultural inoculant throughout the world for more than 25 years (Okon and Labandera-Gonzalez, 1994, Soil Biol. Biochem. 26:1591–1601). Although it is known from the literature that riboflavin synthesis can limit $N_2$-fixation capacity in rhizobia (Pankthurst et al, 1974, Plant Physiol. 53:198–205), there are no published reports on increasing the production of this compound in Rhizobiaceae bacteria. Indeed, no genes in the Rhizobiaceae have been identified as contributing to riboflavin synthesis.

The biosynthetic pathway for riboflavin has been defined (Young, 1986, Nat. Prod. Rpt. 3:395–419), and genes associated with various steps in the pathway have been characterized in *Escherichia coli* (Eberhardt et al, 1996, Eur. J. Biochem. 242: 712–719; Richter et al, 1992, J. Bact. 174:4050–4056; Richter et al, 1997, J. Bact. 179:2022–2028), *Bacillus subtilis* (Coquard et al, 1997, Mol. Gen. Genet. 254:81–84; Perkins and Pero, 1993, In: *Bacillus subtilis* and Other Gram-Positive Bacteria, A. L. Sonenshein et al eds. Amer. Soc. Microbiol. Washington, D.C. p. 319–325; Schott et al, 1990, J. Biol. Chem. 265: 4204–4209), and several other bacteria outside the Rhizobiaceae. Commercial production of riboflavin was facilitated by expressing multiple copies of the rib operon in *B. subtilis* to achieve riboflavin titers of 4.5 g/liter (Stepanov et al, 1984, French patent application 3599355).

The present invention, by providing novel enhancers of net photosynthesis and enhancers of plant growth, particularly enhancers that can be synthesized by microbes and isolated from microbial extracts, fulfills these, and other, needs.

SUMMARY OF THE INVENTION

Compositions and Methods for Enhancing Pant Growth

The present invention provides novel methods to enhance plant growth. Data reported for the first time in this patent application establishes that *Sinorhizobium meliloti*, which is already known to promote plant growth by $N_2$ fixation, also increases plant growth by a mechanism resembling the effect of plant hormones, e.g., by producing plant growth enhancer such as lumichrome. In alternative embodiments, the enhancer applied to the plant is a microorganism, such as a recombinantly engineered microorganism, or, is an isolated or purified composition derived from a microorganism. In alternative embodiments, the compounds are microbial extracts, microbial secretion products, and microbially generated natural products.

The invention provides a method for increasing net growth in a plant comprising applying an agent comprising lumichrome to the plant or seed in an amount effective for increasing net growth in the plant. Application of the agent to the plant includes application to all parts of the plant, including, e.g., seeds, roots, shoots, stems, leaves and the like. In one embodiment, the agent thus applied comprises a microorganism, such as a bacterium, e.g., an endophytic bacterium, a root-colonizing or shoot-colonizing bacterium, or a soil-dwelling bacterium, a soil-dwelling yeast, or a soil-dwelling fungus. The bacterium can be from the family Rhizobiaceae, or a *Rhizobium* spp., a *Bradyrhizobium* spp, a *Sinorhizobium* spp. or a *Pseudomonas* spp. The bacterium, for instance, can be a *Sinorhizobium fredii*, a *Sinorhizobium meliloti*, a *Bradyrhizobium japonicum*, or a *Pseudomonas fluorescens*.

In alternative embodiments, the bacterium can be applied in an aqueous solution in a concentration of about $10^5$ to about $10^{10}$ bacteria per mL or in a concentration of about $10^7$ to about $10^8$ bacteria per mL. The bacterium can release lumichrome at a rate of about 0.5 ng lumichrome/day/$10^7$ cells to about 10 ng lumichrome/day/$10^7$ cells. Alternatively, the agent thus applied in this method can comprise a bacteria culture media.

The agent can have a lumichrome concentration of about 3 nM to about 50 nM. the agent can be applied to the plant in multiple applications, such as, e.g., about every 24 to 48 hours, every 72 hours, every week, and the like.

In various embodiments, the lumichrome is applied to an angiosperm, such as, e.g., a monocotyledonous plant or a dicotyledonous plant. The dicotyledonous plant can be a legume, such as, e.g., an alfalfa The invention also provides a method for increasing net growth in a plant (which includes all parts of the plant, such as seeds, roots, etc.), the method comprising growing the plant or seed in a hydroponic culture system comprising an aqueous medium comprising lumichrome or riboflavin in an amount effective for increasing net growth in the plant. The aqueous medium can have a lumichrome concentration of about 3 nM to about 50 nM or riboflavin concentration of about 20 nM to about 500 nM.

The invention also provides a method for increasing net growth in a plant or seed, the method comprising growing the plant or seed in a controlled solid growth medium comprising a lumichrome-releasing or a riboflavin-releasing microorganism in an amount effective for increasing net growth in the plant. The medium can have about 1 to about 20, about 20 to about 50 or about 50 to about 100 micrograms of lumichrome per gram of medium, or about 10 to about 100 or about 100 to about 500 or about 500 to 1000 micrograms of riboflavin per gram of medium, or a concentration of lumichrome- or riboflavin-releasing microorganisms of about $10^2$ to about $10^5$ or about $10^5$ to about $10^{10}$ bacteria per gram of medium. The medium can be vermiculite, sterile vermiculite, peat, sterile peat, soil, or a sterile soil. The plant grown in the controlled growth medium can be a legume. The plant can be growing in a medium under field conditions and the microorganism is inoculated onto the plant or seed or in the medium. In alternative embodiments, the microorganism can be a *Sinorhizobium meliloti* bacterium and the host plant is an alfalfa (*Medicago sativa*); the microorganism can be a *Bradyrhizobium japonicum* bacterium and the host plant is a soybean (*Glycine max*); the microorganism can be a *Sinorhizobium fredii* bacterium and the host plant is a soybean (*Glycine max*).

The invention also provides a method for increasing net growth in a plant, the method comprising applying to said plant an agent comprising a riboflavin-releasing or a lumichrome-releasing microorganism, wherein the microorganism is applied in an amount effective to increase net growth in the plant. The microorganism thus applied can be selected or genetically engineered to release greater than wild type levels of lumichrome or riboflavin. The microorganism can release lumichrome or riboflavin at a rate of about 0.1, 0.5, 1, 2, 5, 10, 20, 30, 50, 100, 500 or 1000 ng lumichrome or riboflavin/day/$10^7$ cells to about 2000 ng lumichrome or riboflavin/day/$10^7$ cells.

In alternative embodiments, the microorganism thus applied can be an endophyte or a soil-dwelling microorganism or a bacterium. In this method, the bacteria can be a *Sinorhizobium meliloti* bacterium and the host plant a *Medicago* spp.; or, the bacterium can be a *Bradyrhizobium japonicum* bacterium and the host plant a *Glycine max*; or, the bacterium can be a *Sinorhizobium fredii* bacterium and the host plant a *Glycine max*. The bacterium can be from the family Rhizobiaceae, a *Rhizobium* spp., a *Bradyrhizobium* spp, a *Sinorhizobium* spp. or a *Pseudomonas* spp. The bacterium can be a *Sinorhizobium fredii*, a *Sinorhizobium meliloti*, a *Bradyrhizobium japonicum*, or a *Pseudomonas fluorescens*. The microorganism thus applied can be a fungus, such as, e.g., an *Aspergillus*, a *Glomus*, a *Gigaspora*, or a *Scutellospora*. The microorganism thus applied can be a yeast, such as, e.g., a *Candida*.

In this method, the bacterium thus applied can be in an aqueous solution in a concentration of about $10^5$ to about $10^{10}$ bacteria per mL or at a concentration of about $10^7$ to about $10^8$ per mL. The microorganism thus selected or genetically engineered can produce greater than wild-type levels of riboflavin synthase or a protein effecting synthesis of riboflavin. The genetically engineered microorganism can be transduced (i.e., stably transfected) with an expression cassette (e.g., recombinant vector, plasmid, virus) comprising a nucleic acid comprising a sequence substantially identical to a *Sinorhizobium meliloti* genomic sequence located in the ~4248 base pair EcoRI insert of plasmid pribD/C1 (SEQ ID NO:1). The genomic sequence located in the ~4248 base pair EcoRI insert of plasmid pribD/C1 (SEQ ID NO:1) can be substantially identical to or substantially complementary to SEQ ID NO:1.

In another embodiment, the genetically engineered microorganism has been transduced with an expression cassette comprising a nucleic acid encoding and expressing a riboflavin synthesis gene, such as, e.g., a coding sequence from a ribC or a ribD open reading frame. The ribC open reading frame can be from *Escherichia coli* or *Sinorhizobium meliloti*. The ribC *Sinorhizobium meliloti* open reading frame can comprise a sequence substantially identical to SEQ ID NO:2. The ribD *Sinorhizobium meliloti* open reading frame can comprise a sequence substantially identical to SEQ ID NO:4.

The invention also provides an isolated or recombinant nucleic acid comprising a sequence substantially identical to or substantially complementary to the *Sinorhizobium meliloti* genomic sequence located in the ~4248 base pair EcoRI insert of plasmid pribD/C1 (SEQ ID NO:1). This genomic sequence can be substantially identical to or substantially complementary to SEQ ID NO:1. Also provided is an expression cassette comprising the a sequence substantially identical to or substantially complementary to the *Sinorhizobium meliloti* genomic sequence located in the ~4248 base pair EcoRI insert of plasmid pribD/C1 (SEQ ID NO:1); and, a transformed cell comprising this nucleic acid or expression cassette (e.g., recombinant vector, plasmid, virus).

The invention further provides an isolated nucleic acid comprising a nucleic acid sequence: having at least 65% sequence identity to SEQ ID NO:2 or a nucleic acid encoding a polypeptide, wherein the polypeptide has a sequence as set forth in SEQ ID NO:3; or, having at least 65% sequence identity to SEQ ID NO:4 or a nucleic acid encoding a polypeptide, wherein the polypeptide has a sequence as set forth in SEQ ID NO:5; or, having at least 65% sequence identity to SEQ ID NO:6 or a nucleic acid encoding a polypeptide, wherein the polypeptide has a sequence as set forth in SEQ ID NO:7; or, having at least 65% sequence identity to SEQ ID NO:8 or a nucleic acid encoding a polypeptide, wherein the polypeptide has a sequence as set forth in SEQ ID NO:9; or, having at least 65% sequence identity to SEQ ID NO:10 or a nucleic acid encoding a polypeptide, wherein the polypeptide has a sequence as set forth in SEQ ID NO:11; or, which specifically hybridizes to SEQ ID NO:2 or SEQ ID NO:4 or SEQ ID NO:6 or SEQ ID NO:8 or SEQ ID NO:10 under stringent conditions, wherein the stringent conditions comprise at least one wash step using a solution comprising: a salt concentration of about 0.02 molar at pH 7 and a temperature of at least about 60° C., or a salt concentration of about 0.15 M NaCl at a temperature of about 72° C. for about 15 minutes; or, a salt concentration of about 0.2×SSC at a temperature of at least about 50° C. for about 15 minutes; or a salt concentration of about 2×SSC containing 0.1% SDS at room temperature for 15 minutes followed by a salt concentration of about by 0.1×SSC containing 0.1% SDS at 68° C. for 15 minutes; or, equivalent conditions. Also provided is a polypeptide encoded by a nucleic acid of the invention.

In alternative embodiments, the sequence identity to SEQ ID NO:2 or SEQ ID NO:4 or SEQ ID NO:6 or SEQ ID NO:8 or SEQ ID NO:10 is at least 75%; the sequence identity to SEQ ID NO:2 or SEQ ID NO:4 or SEQ ID NO:6 or SEQ ID NO:8 or SEQ ID NO:10 is at least 85%; the sequence identity to SEQ ID NO:2 or SEQ ID NO:4 or SEQ ID NO:6 or SEQ ID NO:8 or SEQ ID NO:10 is 95%; or, the nucleic acid comprises a sequence as set forth in SEQ ID NO:2 or SEQ ID NO:4 or SEQ ID NO:6 or SEQ ID NO:8 or SEQ ID NO:10. Also provided is an expression cassette comprising at least one of these nucleic acids operably linked to a transcriptional regulatory sequence, e.g., a promoter, an enhancer, and the like; and, a transformed cell comprising at least one of these nucleic acids or expression cassettes of the invention.

The transformed cell can be a microorganism, such as, e.g., a soil-dwelling or a plant endophytic microorganism. The transformed cell can be a bacterium. The bacterium can be from the family Rhizobiaceae, a *Rhizobium* spp., a *Bradyrhizobium* spp, a *Sinorhizobium* spp. or a *Pseudomonas* spp. The bacterium can be a *Sinorhizobium fredii*, a *Sinorhizobium meliloti*, a *Bradyrhizobium japonicum*, or a *Pseudomonas fluorescens*. Alternatively, the microorganism can be a fungus or a yeast. The fungus can be an *Aspergillus*, a *Glomus*, a *Gigaspora*, or a *Scutellospora*.

The invention also provides polypeptides having at least 65% sequence identity, at least 75% sequence identity, at least 85% sequence identity, at least 95% sequence identity or 100% sequence identity to SEQ ID NO:3, SEQ ID NO:5, SEQ ID NO:7, SEQ ID NO:9 and SEQ ID NO:11.

The invention also provides antibodies (including antisera, isolated polyclonal antibodies, and monoclonal antibodies and their hybridomas) which specifically bind to the polypeptides of the invention.

Methods for Identifying Enhancers of Net Photosynthesis

The present invention also provides novel methods for identifying new enhancers of net photosynthesis in a plant. Enhancers are identified by analyzing the effect of test compounds on a plant. The test compound comprises extracts derived from microorganisms, such as a bacterial, fungi, or yeast. In one embodiment, the bacterial extract can be a microbial secretion product. In a preferred embodiment, the methods include measuring respiration in the root of the plant.

In one embodiment, the invention provides a method for identifying enhancers of net photosynthesis in a plant by contacting the plant with a test compound comprising a microbial extract; followed by measuring an increase in net photosynthesis in the plant attributable to said bacterial extract (i.e., observing the plant to determine whether there is an increase in net photosynthesis in the plant attributable to said bacterial extract). The increase in net photosynthesis can be measured over minutes, hours or days. In a preferred embodiment, the test compound is applied to the root of the plant. Microbial extract can be derived from any microorganism, such as, e.g., a bacterium, yeast, alga or fungus. The bacterial extract can also be a secretion product of the microorganism.

In the methods of the invention, after application of the test compound to the plant, an increase in net photosynthesis can be measured by any means, including, e.g., by measuring a net increase in carbon dioxide gas uptake by the plant; by measuring a net increase in the uptake of radioisotope $^{14}C$ by the plant; by measuring a net increase in oxygen ($O_2$) generated by the plant; by measuring a net increase in carbon assimilation in the plant; by measuring a net increase in plant photosynthates; by measuring a net increase in dry weight of the plant. In a preferred embodiment, carbon assimilation is measured in the shoots or leaves of the plant.

As noted above, in a preferred embodiment, the methods can further include measuring an increase in delayed respiration in the root of the plant. Delayed root respiration can be measured by any means, including, e.g., measuring a net increase in oxygen ($O_2$) absorbed by the plant, or measuring an increase in carbon dioxide gas generated by the plant, both of which can be measured by gas chromatography, as described in detail, below.

A further understanding of the nature and advantages of the present invention may be realized by reference to the remaining portions of the specification and claims.

All publications, GenBank Accession references (sequences), ATCC Deposits, patents and patent applications cited herein are hereby expressly incorporated by reference for all purposes.

DETAILED DESCRIPTION OF THE INVENTION

Compositions and Methods for Enhancing Plant Growth

This invention is a first description of novel, bacterially derived, enhancers of net photosynthesis and novel means to enhance plant growth. Use of enhancers of net photosynthesis and plant growth from microbial sources confers many advantages, especially in the production of the reagents and their application to plants and crops. As natural products, the photosynthetic and growth enhancers can be produced on a large, economical scale using conventional industrial techniques. The enhancers of net photosynthesis and growth can be applied to the plant in a growth-controlled environment, such as a hydroponic growth or controlled growth culture system (e.g., using vermiculite). Alternatively, the seeds of a plant can be exposed to the enhancing agents before and/or during germination.

In one embodiment, the enhancer is administered to the plant by application of a bacterium that releases the growth-enhancing agent. Bacteria applied to the plant in the methods of the invention can be strains that have been selected for over-production of the enhancing agent, e.g., riboflavin or lumichrome. Alternatively, bacteria applied to the plant in the methods of the invention can be strains that have been genetically engineered and selected for over-production of a growth-enhancing agent, e.g., riboflavin or lumichrome.

In one embodiment, recombinant bacteria comprising all or part of the ribC/ribD gene complex of the invention and expressing the ribC and/or the ribD open reading frames (ORFs) (SEQ ID NO:2 and SEQ ID NO:4, respectively) and gene products (SEQ ID NO:3 and SEQ ID NO:5, respectively) are used in the methods of the invention to overexpress riboflavin or lumichrome. The complex comprises nucleic acid sequence as set forth in the ~4.25 kilobase EcoRI fragment (SEQ ID NO:1) isolated from *Sinorhizobium meliloti* 1021.

The ribC and/or the ribD ORFs encode a riboflavin synthase enzyme which, when inserted into a microorganism in an appropriate expression system, drive increased expression of endogenous riboflavin synthase to generate an increase release of riboflavin and/or lumichrome by the microorganism. In one embodiment, the ORFs of the ribC and/or the ribD genes are incorporated in expression cassettes, e.g., plasmids, recombinant vectors or viruses for expression in the recombinant microorganisms of the invention. The ORFs of the ribC and/or the ribD genes (SEQ ID NO:3 and SEQ ID NO:5, respectively) can be operably linked to a transcriptional regulatory sequence, e.g., a promoter or enhancer, that drives constitutive or inducible expression in bacteria or other cells. The transcriptional regulatory sequence can be heterologous, e.g., a viral or bacterial promoter, or can be endogenous, e.g., a *Sinorhizobium meliloti* ribC and/or the ribD promoter or enhancer, which can include any sequence from the ~4.25 kilobase EcoRI fragment (the complementary strand with respect to the ORFs is SEQ ID NO:1).

The invention provides various concentrations and levels of purity of these novel enhancers of net photosynthesis. For example, the bacteria known to produce the enhancers of the invention (e.g., lumichrome or riboflavin) can be directly applied to a plant, e.g., the roots, shoots, leaves, seeds. Alternatively, the enhancer can be isolated (term defined below) before applying to the plant. As used herein, such isolation includes substantially pure enhancing reagents, relatively crude preparations, and any variation thereof, as long as the preparation has the ability to enhance net photosynthesis or plant growth. If the enhancer is secreted into a microbial culture medium, the medium itself can be applied, or, it may only be necessary to concentrate the medium. Thus, significant quantities of active reagent can be produced and used without the need for substantial purification or structural characterization of the active chemical entity in the identified natural product.

The level of purity or concentration of an enhancer of net photosynthesis or plant growth of the invention needed for a particular situation may vary depending on, e.g., what plants (or seeds) are being treated, where and how the plants are treated (e.g., spraying on leaves, liquid application to soil, hydroponic cultures (e.g., Wang (1996) *Biol. Trace Elem. Res.* 55:147–62; Ling (1993) *J. Chromatogr.* 643:351–5), "aeroponic" growth on moistened filter paper in Petri dishes (e.g., Tari (1990) *Acta Biol Hung* 41:387–97) growth in nutrient solution-circulating growth chambers (e.g., Shima (1997) *Mutat Res* 1997 December 12;395(2–3): 199–208), injections into the plant), soaking seeds, and the like, which can be determined by the skilled artisan with routine screening and testing.

Being bacterial natural products, significant quantities of an enhancer of the invention can be identified, produced and used without the need for purification to homogeneity or structural characterization. Furthermore, if the microorganism producing an enhancer of the invention can grow in soil or can colonize the plant (e.g., roots, shoots, leaves), application of the microbe to the soil, controlled growth medium (e.g., comprising vermiculite) or a liquid growth medium (e.g, hydroponics).would be sufficient to enhance net photosynthesis or plant growth. For example, in alternative embodiments, microorganisms, e.g., bacteria, yeast, fungi, the recombinant microorganisms of the invention, which release riboflavin or lumichrome are applied to the root, shoot, leaves or seeds of a plant in amounts sufficient to increase net growth of the plant.

The active plant growth-enhancing reagent can be purified and/structurally identified. Its biosynthetic pathway and the genetic mechanisms responsible for producing the bioactive agent by the microbe can be found. Using this information, genetically engineered (e.g., transformed or transgenic) microorganisms capable of synthesizing the plant growth enhancers of the invention are constructed. Thus, any soil-borne or plant (e.g., root, shoot, leaf, seed)-colonizing microorganism can be recombinantly manipulated to generate an enhancer of net photosynthesis or plant growth.

In an alternative embodiment, the invention provides a novel method for increasing net photosynthesis in a plant by applying an agent containing triacetylphloroglucinol, diacetylphloroglucinol, or monoacetylphloroglucinol to the plant in an amount effective for increasing net photosynthesis in the plant. These agents can be applied to the plant in a controlled growth setting, e.g., in a hydroponic or vermiculite-based growth medium These enhancers (also including lumichrome, riboflavin) of net photosynthesis can also be synthesized as natural products by microorganisms, particularly bacteria, and used with the advantages described above.

However, it is not necessary that the enhancers of the invention be natural products of microbes. In one embodiment, the enhancers of net photosynthesis are organically synthesized, as described below.

Methods for Identifying Enhancers of Net Photosynthesis

This invention is a first description of methods to identify enhancers of plant photosynthesis using the natural products of microorganisms. Thus, the methods of the invention provide novel means to identify potential enhancers of net photosynthesis from a richly diverse, yet unexploited natural source. The methods of the invention utilize all families and genera of microorganism, including, e.g., bacteria, algae, fungi.

As discussed above, identification of photosynthetic enhancing reagents from microorganisms confers many advantages, especially in the production of the enhancer as a natural product and its application to plants and crops. For example, as a natural product, the newly identified photosynthetic enhancer can be produced on a large, economical scale using conventional industrial techniques.

The methods of the invention can also be used to determine what concentrations and levels of purity of reagent are needed to enhance photosynthesis. For example, the methods will determine if it is necessary, and to what degree, the enhancing reagent should be purified to attain the desired increase in net photosynthesis. For example, the methods can determine if a relatively crude preparation can be used to enhance photosynthesis. If the enhancer is secreted into culture medium, it may suffice to apply the medium directly to the plant without further purification. Alternatively, it may only be necessary to concentrate the medium. Thus, significant quantities of active reagent can be produced and used without the need for purification to homogeneity or structural characterization of the net photosynthesis-enhancing natural product.

The level of purity or concentration of photosynthetic enhancer may vary depending on, e.g., what plants are being treated, where and how the plants are treated (e.g., spraying on leaves, liquid application to soil, hydroponic cultures (e.g., Wang (1996) *Biol. Trace Elem. Res.* 55:147–62; Ling (1993) *J. Chromatogr.* 643:351–5), "aeroponic" growth on moistened filter paper in Petri dishes (e.g., Tari (1990) *Acta Biol Hung* 41:387–97) growth in nutrient solution-circulating growth chambers (e.g., Shima (1997) *Mutat Res* 1997 December 12;395(2–3):199–208), injections into the plant, and the like.

In an alternative embodiment, the invention provides a method for identifying a photosynthetic enhancing reagent by applying a microorganism to the plant. In this way, panels of different organisms can be rapidly screened for their ability to increase net photosynthesis. If the microorganism can grow in soil or can colonize the plant (e.g., roots, leaves), application of the microbe to the soil in the field could be sufficient to enhance net photosynthesis.

In one embodiment, measurement of root respiration is the first measurement taken after application of the test compound to the plant. This embodiment involves applying a test compound and measuring an increases in root respiration in conjunction with measuring net photosynthesis. Increases in "delayed" root respiration are frequently correlated with net increases in photosynthesis in the plant. Thus, in this embodiment, if a test compound, after application to the plant, results in a net increase in root respiration in the plant, then the test compound has been tentatively identified as an enhancer of net photosynthesis in the plant.

While there is not an absolute correlation between an increase in root respiration and a net increase in photosynthesis, compositions that cause an "delayed" increase in root respiration are also frequently enhancers of net photosynthesis in a plant. Basically, photosynthates, generated by a net increase in photosynthesis caused by application of a photosynthesis enhancing reagent, are transported to the root to drive an increase in respiration. The transport of this newly generated photosynthate to the roots typically takes about two to four hours. Thus, a "delayed" increase in root respiration is a secondary effect of an increase in net photosynthesis (with increased photosynthate production) in the plant.

For example, some molecules cause a rapid increase (e.g., within 15 minutes) in root respiration, while others, like the photosynthesis-enhancing *Rhizobium* natural compound D, identified by the methods of the invention (described below), produce a slower increase (greater than 4 hours) in root respiration. As explained above, a rapid increase in respiration cannot be explained by a change in net photosynthesis (i.e., generation of new photosynthates) because it takes a plant about 3 hours to transport photosynthate to the root. However, if the test compound causes a "slow" or "delayed" (greater than about two to about four hours) increase in root respiration, it typically is doing so by causing an increase in net photosynthesis.

In one embodiment, root respiration is measured by the generation of carbon dioxide gas by the root, or, alternatively, by a net assimilation of oxygen gas from the plant. This gas exchange can be measured, e.g., by gas chromatograph, as described in detail, below.

In alternative embodiments, net photosynthesis in the plant is determined first, concurrently or after measuring for net increase in root respiration. Net increase in photosynthesis can be determined by a variety of means, including, e.g., net increase in carbon dioxide (e.g., radioisotope $^{14}C$-containing) gas uptake by the plant, measuring a net increase in oxygen ($O_2$) generated by the plant, or measuring a net increase in carbon assimilation in the plant. The latter can be determined by, e.g., measuring a net increase in plant photosynthates or measuring a net increase in dry weight of the plant.

If the active reagent is identified, biosynthetic and genetic mechanisms responsible for producing the bioactive agent by the microbe can also be found. Transgenic microorganisms capable of synthesizing the enhancer identified by the methods of the invention can then be constructed. Thus, any soil-borne or plant (e.g., shoot, root (rhizosphere), leaf)-colonizing microorganism can be recombinantly manipulated to generate the photosynthetic enhancing agent discovered using the methods of the invention.

Definitions

To facilitate understanding the invention, a number of terms are defined below.

As used herein, the terms "isolated" or "isolate," when referring to a molecule or compound, such as, e.g., an extract or isolate from a microorganism, such as a bacterium, means that the molecule or composition is separated from at least one other compound, such as a protein, a sugar, a lipid, a nucleic acid (e.g., RNA, DNA), or other contaminants with which it is associated in vivo or in its naturally occurring state. Thus, an enhancer of net photosynthesis of the invention is considered isolated when it has been separated from at least one other component with which it is associated in vivo or in vitro, e.g., cell membrane, as in a cell extract, or from a culture media into which the compound had been secreted by a microbe. For example, enhancers of net photosynthesis as bacterial products are isolated to varying degrees of purity using column chromatography and high performance liquid chromatography (HPLC), as described below. Furthermore, an isolated enhancer of the invention can also be substantially pure. An isolated composition can be in a homogeneous state and can be in a dry or an aqueous solution. Purity and homogeneity can be determined, e.g., using analytical chemistry techniques such as polyacrylamide gel electrophoresis (SDS-PAGE) or HPLC; or, using biological assays, particularly, by testing an extract for its ability to increase net photosynthesis using the methods of the invention.

As used herein, the terms "bacterium" and "bacteria" incorporate their common usage, and includes, e.g., all genera and species from the Prokaryotae (Monera) Kingdom (e.g., bacteria, including Eubacteria and Archeabacteria), as described in further detail below. The methods of the invention include application of any microorganism that can generate a net photosynthesis-enhancing agent of the invention, including, e.g., *Sinorhizobium meliloti* (also known as *Rhizobium meliloti*), and *Pseudomonas fluorescens* (see Examples, below). As used herein, the term "bacterial product" incorporates its common usage, and includes, e.g., any and all compositions associated with (e.g., generated or synthesized by) a bacteria, internal or external or secreted, including the entire bacterium.

The term "net increase in dry weight" in a plant, as used herein, incorporates its common usage; means to determine the dry weight of a plant are well known, see, e.g., Berkelar (1 996) *Photochem. Photobiol*. 64:110–6; Slater (1975) Arch Microbiol. 103:45–9; and discussion below.

The term "expression cassette" refers to any recombinant expression system for the purpose of expressing a nucleic acid sequence of the invention in vitro or in vivo, constitutively or inducibly, in any cell, including, in addition to plant cells, prokaryotic, yeast, fungal, insect or mammalian cells. The term includes linear or circular expression systems. The term includes all vectors. The cassettes can remain episomal or integrate into the host cell genome. The expression cassettes can have the ability to self-replicate or not, i.e., drive only transient expression in a cell. The term includes recombinant expression cassettes which contain only the minimum elements needed for transcription of the recombinant nucleic acid; e.g., a polypeptide coding sequence operatively linked to a promoter. The phrase "operably linked" refers to a functional relationship between two or more nucleic acid (e.g., DNA) segments. Typically, it refers to the functional relationship of a transcriptional regulatory sequence to a transcribed sequence. For example, a promoter (defined below) is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. For example, in one embodiment, a promoter is operably linked to a nucleic acid ORF sequence of the invention, as exemplified by SEQ ID NO:2, SEQ ID NO:4, SEQ ID NO:8, SEQ ID NO:10 and SEQ ID NO:12.

As used herein, the term "genetically engineered" includes any modification of the wild type genomic sequence by genetic engineering (versus only selective pressure) techniques, including, e.g., the generation of deletions, mutations, insertions, changes in expression (transcription or translation) levels or rates, and the like.

As used herein, the terms "monoacetylphloroglucinol," "diacetylphloroglucinol," and "triacetylphloroglucinol," incorporate their broadest chemical meaning. Diacetylphloroglucinol has the chemical formula $C_{10}H_{10}O_5$. One form of diacetylphloroglucinol is 2,4-diacetylphloroglucinol, also known as 2,4diacetyl-1,3,5-benzenetriol.

As used herein, the term "increase in net photosynthesis" means that, over a time period, more photosynthesis than respiration (including the sum of photorespiration and dark respiration) occurs in the plant as a whole. A variety of means are available to the skilled artisan for evaluating and measuring a net increase in photosynthesis in a plant in practicing the methods of the invention. For example, if there is an increase in net photosynthesis, then the increase in the amount of oxygen gas released from the plant is greater than the increase in the amount of carbon dioxide gas released (which is, as discussed below, detectable and quantifiable). Furthermore, if there is an increase in net photosynthesis, the plant normally increases its biomass, which can be determined by, e.g., measuring an accumulation of photosynthates or an increase in plant "dry weight." However, the increase in biomass generated by the net increase in the photosynthetic reaction may not be uniform throughout the plant or may be transient For example, when increased amounts of photosynthate (generated by net increase in photosynthesis) are transported to the roots and used to drive an increase rate of dark respiration in the root, the photosynthates are consumed in the dark respiration reaction; they are not used to increase the dry weight (biomass) of the root. Thus, the term "enhancer of net photosynthesis" indicates that a composition, an extract, a microorganism, can increase net photosynthesis in a plant, as can be determined by methods described herein. The compositions of the invention can be identified and evaluated by determining their ability to increase net photosynthesis in a plant using these routine tests.

As used herein, the term "increase in net plant growth" means that, over a time period, a plant treated with a method of the invention as a whole increases its biomass in an amount greater than the plant would have grown under identical conditions without application of the method. The increase in biomass can be isolated to a particular plant part, e.g., the roots, shoots, leaves, or seeds, or can be distributed throughout the entire plant This can be determined by, e.g., measuring an accumulation of radioactive carbon or an increase in plant "dry weight," as discussed herein.

As used herein, the term "inoculating," as in inoculating a plant or seed, includes any technology that can deliver a microorganism, particularly a bacteria, e.g., of the family Rhizobiaceae, to a host plant, particularly a legume host plant for the purpose of forming root nodules and reducing elemental nitrogen ($N_2$) to ammonia As used herein, the term "microorganisms" is used in its common context and includes, e.g., all bacteria (see above definition), yeast, protista, and fungi.

As used herein, the terms "nucleic acid" and "polynucleotide" are used interchangeably, and include oligonucleotides (i.e., short polynucleotides). The terms also refer to synthetic and/or non-naturally occurring nucleic acids (i.e., comprising nucleic acid analogues or modified backbone residues or linkages). The terms also refer to deoxyribonucleotide or ribonucleotide oligonucleotides in either single-stranded (including the sense or antisense strands) or double-stranded form. The terms encompass nucleic acids containing known analogues of natural nucleotides. The terms also encompass nucleic-acid-like structures with synthetic backbones, as discussed below.

As used herein, the term "plant" includes whole plants, plant organs (e.g., leaves, stems, flowers, roots, etc.), plant protoplasts, seeds and plant cells and progeny of same. The class of plants which can be used in the method of the invention includes angiosperms (monocotyledonous and dicotyledonous plants), as well as gymnosperms. It includes plants of a variety of ploidy levels, including polyploid, diploid, haploid and hemizygous (see discussion, infra).

The term "plant photosynthate" incorporates its common usage, and, as used herein, includes polysaccharides (e.g., starch, carbohydrates), oligosaccharides (e.g. sucrose, a disaccharide) and monosaccharides. In the methods of the invention, an increase in the amount of photosynthates in the plant after applying a test compound indicates that the compound has increased net photosynthesis in the plant As used herein, when referring to a "polypeptide" sequence, the sequence includes all variations with "conservative amino acid" substitutions or variations. "Conservative substitution" refers to a change in the amino acid composition of a protein, such as the polypeptides of the invention, that does not substantially alter the protein's activity. This includes conservatively modified variations of a particular amino acid sequence, i.e., amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids does not substantially alter activity. Thus, a polypeptide sequence of the invention implicitly, and expressly, as defined herein, encompasses conservatively substituted variants thereof Conservative substitution tables providing functionally similar amino acids are well known in the art. The following six groups each contain amino acids that are conservative substitutions for one another: 1) Alanine (a), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see also, Creighton (1984) Proteins, W.H. Freeman and Company). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions which alter, add or delete a single amino acid or a small percentage of amino acids in an encoded sequence can also be considered "conservatively modified variations."

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells. Such a promoter can be derived from plant genes or from other organisms, such as viruses capable of infecting or replicating in plant cells.

Ther term "Rhizobiaceae" refers to the family consisting of a heterogeneous group of gram-negative, aerobic, non-spore-forming rods that can invade and induce a highly differentiated structure, the nodule (on the roots, and in some instances, stems of leguminous plants), within which atmospheric nitrogen is reduced to ammonia by the bacteria It is currently recognized that the family Rhizobiaceae contains at least six genera, *Rhizobium, Bradyrhizobium, Sinorhizobium, Mesorhizobium, Allorhizobium* and *Azorhizobium*. The host plant is most often of the family Leguminosae (i.e., legumes). The slow-growing nodulation bacteria which have specific associations with soybean are referred to as *Bradyrhizobium*, such as *B. japonicum*. Some soybean plants can also nodulate with the fast growing *Rhizobium fredii*. *Rhizobium* species, sometimes designated "fast-growing" rhizobia, include, e.g., *S. meliloti* which infects alfalfa.

As used herein, the terms "ribC," "ribD," "ribBA," "glyA" and "ribH" include the wild type and all homologues and variations of the wild-type ribC, ribD, ribBA, glyA and ribH genes, transcription products, and related nucleic acid sequences and the wild-type RibC, RibD, RibBA, GlyA and RibH gene products (polypeptides), respectively. "RibC," "ribD," "ribBA," "glyA" and "ribH" polynucleotide sequences are exemplified by SEQ ID NO:2, SEQ ID NO:4, SEQ ID NO:8, SEQ ID NO:10, and SEQ ID NO:12.

The terms above also include polymerase chain reaction (PCR)-amplified products. Thus, PCR can be used to amplify, e.g., *S. meliloti* polynucleotide sequences, with the use of primers selected from the ends of a particular gene sequence. For instance, primers SEQ ID NO:14 and SEQ ID NO:15 can be used to amplify ribC polynucleotide sequences. Primers SEQ ID NO:16 and SEQ ID NO:17 can be used to amplify ribD polynucleotide sequences. Primers SEQ ID NO:18 and SEQ ID NO:19 can be used to amplify glyA polynucleotide sequences. Primers SEQ ID NO:20 and SEQ ID NO:21 can be used to amplify ribBA polynucleotide sequences. Primers SEQ ID NO:22 and SEQ ID NO:23 can be used to amplify ribH polynucleotide sequences. Moreover, such amplified sequences can be used as probes to identify polynucleotides of the invention. For a general overview of PCR, see *PCR Protocok: A Guide to Methods and Applications*. (Innis, M, Gelfand, D., Sninsky, J. and White, T., eds.), Academic Press, San Diego (1990).

The ribC and "ribD" genes include all transcriptional and translation control elements, which can include sequence from any part of the 4.248 kilobase (kb) insert from the plasmid designated pribD/C1 (nucleic acid sequence of complementary strand (with respect to ORFs) is SEQ ID NO:1). The ribC *Sinorhizobium meliloti* ORF comprising SEQ ID NO:2 (coding strand) is described for the first time herein. The ribD *Sinorhizobium meliloti* ORF comprising SEQ ID NO:4 (coding strand) is described for the first time herein. The *Escherichia coli* ribC gene for riboflavin synthase is available as ATCC accession numbers X69109 and X79488, see also Eberhardt (1996) Eur. J. Biochem. 242:712–719. See also Gusarov (1997) Mol. Biol. 31:446–453. RibC and RibD play essential roles in flavin metabolism in microorganisms. An increase in ribC or ribD gene expression and riboflavin synthase activity leads to an increase in riboflavin and lumichrome biosynthesis and release.

As used herein, the term "a protein effecting synthesis of riboflavin" includes any protein, e.g., enzyme or transcriptional regulatory agent which modulates expression of such proteins, the effects the anabolism or catabolism of riboflavin, including, e.g., RibC, RibD, RibBA, RibH or GlyA.

As used herein, the "sequence" of a gene (unless specifically stated otherwise) or nucleic acid refers to the order of nucleotides in the polynucleotide, including either or both strands (sense and antisense) of a double-stranded DNA molecule, e.g., the sequence of both the coding strand and its complement, or of a single-stranded nucleic acid molecule (sense or antisense). For example, in alternative embodiments, promoters drive the transcription of sense and/or antisense polynucleotide ORF sequences of the invention, as exemplified by SEQ ID NO:2, SEQ ID NO:4, SEQ ID NO:8, SEQ ID NO:10, SEQ ID NO:12.

The terms "identical" or percent "sequence identity," in the context of two or more nucleic acids or polypeptide sequences, refer to two or more sequences or subsequences that are the same or have a specified percentage of nucleotides (or amino acid residues) that are the same, when compared and aligned for maximum correspondence over a comparison window, as measured using one of the following sequence comparison algorithms or by manual alignment and visual inspection. This definition also refers to the complement (i.e., complementary, or antisense strand) of a sequence. For example, in alternative embodiments, nucleic acids within the scope of the invention include those with a nucleotide sequence identity that is at least about 60%, at least about 65%, at least about 70%, at least about 75%, at least about 80%, at least about 85%, at least about 90%, and at least about 95% of the exemplary sequences set forth in SEQ ID NO:1, SEQ ID NO:2, SEQ ID NO:4, SEQ ID NO:8, SEQ ID NO:10, and SEQ ID NO:12. In alternative embodiments, polypeptides within the scope of the invention include those with an amino acid sequence identity that is at least about 60%, at least about 65%, at least about 70%, at least about 75%, at least about 80%, at least about 85%, at least about 90%, and at least about 95% of the exemplary sequences set forth in SEQ ID NO:3, SEQ ID NO:5, SEQ ID NO:9, SEQ ID NO:11, and SEQ ID NO:13. Two sequences with these levels of identity are "substantially identical" and within the scope of the invention. Thus, if a nucleic acid sequence has the requisite sequence identity to SEQ ID NO:1, SEQ ID NO:2, SEQ ID NO:4, SEQ ID NO:8, SEQ ID NO:10, and SEQ ID NO:12, or a subsequence thereof, it also is a polynucleotide sequence within the scope of the invention. If a polypeptide sequence has the requisite sequence identity to SEQ ID NO:3, SEQ ID NO:5, SEQ ID NO:9, SEQ ID NO:11, and SEQ ID NO:13, or a subsequence thereof, it also is a polypeptide within the scope of the invention. Preferably, the percent identity exists over a region of the sequence that is at least about 25 nucleotides or amino acid residues in length, more preferably over a region that is at least about 50 to 100 nucleotides or amino acids in length. All necessary parameters (including, e.g., window sizes, gap penalties and the like) to be used in calculating "percent sequence identities" between two nucleic acids or polypeptides (one exemplary and one under analysis) to identify and determine whether the analyzed sequence is within the scope of the invention, are described in detail, below.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention (e.g., is substantially identical to SEQ ID NO:1, SEQ ID NO:2, SEQ ID NO:4, SEQ ID NO:8, SEQ ID NO:10, or SEQ ID NO:12) by its ability to hybridize under stringent conditions to a nucleic acid otherwise determined to be within the scope of the invention (such as the exemplary sequences described herein).

The phrase "stringent hybridization conditions" refers to conditions under which a probe will primarily hybridize to its target subsequence, typically in a complex mixture of nucleic acid, but to no other sequences in significant amounts (a positive signal (e.g., identification of a nucleic acid of the invention) is about 10 times background hybridization). Stringent conditions are sequence-dependent and will be different in different circumstances. Longer sequences hybridize specifically at higher temperatures. An extensive guide to the hybridization of nucleic acids is found in e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Generally, stringent hybridization conditions are selected to be about 5 to 10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent hybridization conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide, as described in Sambrook.

For selective or specific hybridization, a positive signal (e.g., identification of a nucleic acid of the invention) is about 10 times background hybridization. "Stringent" hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include a hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

Exemplary "moderately stringent hybridization conditions" include a hybridization in a buffer of 40% formamide, 1 M NaCl, and 1% SDS at 37° C., and a wash in 1×SSC at 45° C. Those of ordinary skill will readily recognize that alternative but comparable hybridization and wash conditions can be utilized to provide conditions of similar stringency, see, e.g., Sambrook, Tijssen and Ausubel.

Nucleic acids which do not hybridize to each other under moderately stringent or stringent hybridization conditions are still substantially identical if the polypeptides which they encode are substantially identical. This may occur, e.g., when a copy of a nucleic acid is created using the maximum codon degeneracy permitted by the genetic code, as discussed herein (see discussion on "conservative substitutions").

Determining Net Photosynthesis and Growth in a Plant

The invention provides novel methods and compositions for increasing net photosynthesis and growth in a plant. These methods comprise applying to the plant agents that include triacetylphloroglucinol, diacetylphloroglucinol and monoacetylphloroglucinol, and novel isolated bacterial products of the invention, as described herein. These agents are applied to the plant in amounts effective for increasing net photosynthesis in the plant. The invention also provides a method for increasing growth in a plant by applying a composition comprising lumichrome to the plant in an amount effective for increasing net growth. The invention further provides a method for increasing net growth in a plant by applying riboflavin-releasing or lumichrome-releasing microorganisms in an amount effective for increasing net growth.

To evaluate the levels of purity of an agent or bacterial isolate, the effective amounts of agent or riboflavin- or lumichrome-releasing microorganisms needed for a particular application, the sites and modes of delivery, the frequency of applications needed, and the like, any means of measuring rates and levels of net photosynthesis or plant growth can be used. Such routine testing means are well known in the art and include, e.g., increases in, e.g., dry weight; carbon dioxide uptake, oxygen generation, carbon assimilation, plant storage products, such as, e.g., polysaccharides (e.g., starches), lipids, proteins and the like (depending on the plant type or stage in life cycle).

In practicing the methods of the invention, enhancement of net photosynthesis can also be evaluated by analysis of various steps in the photosynthetic biochemical mechanism. For example, the oxidation (redox) state of photosynthetic metalloproteins can be determined by, e.g., UV absorbance changes.

The methods of the invention incorporate all means of measuring net photosynthesis. Such means are well known in the art and include, e.g., increases in, e.g., dry weight; carbon dioxide uptake, oxygen generation, carbon assimilation, plant storage products, such as, e.g., polysaccharides (e.g., starches), lipids, proteins and the like (depending on the plant type or stage in life cycle). In practicing the methods of the invention, enhancement of net photosynthesis can also be evaluated by analysis of the rates of various steps in the photosynthetic biochemical mechanism. For example, the oxidation (redox) state of photosynthetic metalloproteins can be determined by, e.g., UV absorbance changes.

Measuring Net Increase in Carbon Dioxide Uptake by a Plant

The efficacy of an agent or bacterial isolate or riboflavin- or lumichrome-releasing microorganisms and methods of the invention, or application method, or application regimen, can be evaluated by determining the level of net increase in carbon dioxide ($CO_2$) gas uptake by the plant over a measured time period. In the methods of the invention, if a test compound, after application to the plant, results in a net increase in carbon dioxide ($CO_2$) gas uptake by the plant, then the test compound has been identified as an enhancer of net photosynthesis in the plant. Any means can be used to measure a net increase in carbon dioxide uptake by the plant, such as by gas chromatograph, as described in detail below. See also, e.g., Borjesson (1992) Appl. Environ. Microbiol. 58:2599–2605.

Measuring Net Increase in Oxygen Generated by a Plant

An agent or bacterial isolate or riboflavin- or lumichrome-releasing microorganisms and methods of the invention can be evaluated by determining the level of net increase in oxygen gas ($O_2$) generated by the plant over a measured time period. In the methods of the invention, if a test compound, after application to the plant, results in a net increase in oxygen gas ($O_2$) generated by the plant, then the test compound has been identified as an enhancer of net photosynthesis in the plant. Any means can be used to measure a net increase in oxygen generated by the plant, such as by gas chromatograph, as described in detail below (see Example 1, below). See also, e.g., use of the "Barcroft manometer" (Umbreit, W. W., R. H. Burris, J. F. Stauffer. 1972. Manometric & Biochemical Techniques, p. 111–125); and, Greenbaum, U.S. Pat. No. 4,789,436, describing methods and apparatus for nondestructive in vivo measurement of photosynthesis in plants using oxygen electrodes.

Measuring Net Increase in Radioactive Carbon Uptake by a Plant

An agent or bacterial isolate or riboflavin- or lumichrome-releasing microorganisms and methods of the invention can be evaluated by determining the level of net increase in carbon assimilation by the plant over a measured time period. In the methods of the invention, if a test compound, after application to the plant, results in a net increase in carbon assimilation of the plant over the measured time period, then the test compound has been identified as an enhancer of net photosynthesis in the plant. Any means can be used to measure a net increase in carbon assimilation by the plant. In a preferred embodiment, a net increase in carbon assimilation is measured by a net increase in radioactive carbon (radioisotope $^{14}C$) uptake by a plant, as described, e.g., in the isotopic assay for measuring net photosynthesis with $^{14}CO_2$ in Sheikholeslam (1980) Botanical Gazette 141:48–52 (see Example 1, below). See also, e.g., Andralojc (1994) Biochem J 304:781–6.

Measuring Net Increase in Plant Photosynthates

Another preferred means to determine of there is a net increase in carbon assimilation of the plant over the measured time period is to measure a net increase in plant photosynthate levels. As defined above, plant photosynthates include, e.g., polysaccharides (e.g., starch, carbohydrates), oligosaccharides and monosaccharides. Any means can be used to measure an increase in the different classes and levels of photosynthates. See, e.g., Zhang (1997) Arch Biochem Biophys 343:260–8; Zhang (1997) FEBS Lett 410:126–30.

Measuring Net Increase in Dry Weight of a Plant

An agent or bacterial isolate or riboflavin- or lumichrome-releasing microorganisms and methods of the invention can be evaluated by determining the level of net increase in dry weight by the plant over a measured time period. In the methods of the invention, if a test compound, after application to the plant, results in a net increase in dry weight of the plant, then the test compound has been identified as an enhancer of net photosynthesis in the plant. Any means can be used to measure a net increase in dry weight of the plant, see, e.g., Almazan (1997) *Plant Foods Hum Nutr* 50:259–68.

Any individual part of the plant (e.g., seeds, roots, leaves, stems, flowers, fruits) can be individually analyzed for which various individual constituents accumulate after a net increase in photosynthesis. For example, dry matter, protein, fat, ash, minerals (Ca, Fe, K, Mg, Na, Zn), vitamins (carotene, ascorbic acid, thiamin), and various other chemicals (e.g., acids) can be measured. This data will provide additional information to aid in the use of the enhancers of net photosynthesis of the invention by determining which bioconversion processes are mobilized by the reagent for biomass conversion into food or forms suitable for crop production. See, e.g., Almazan (1997) supra; Hung (1997) *Chemosphere* 35:959–77.

Measuring Photosynthesis

Photosynthesis can be monitored concurrently with any of the above means to measure an increase in net photosynthesis in the plant. Photosynthesis can be measured both before, during and after application of the agent or bacterial isolate of the invention to the plant. Any means known in the art can be used. For example, photosynthesis can be evaluated by measuring the redox state of a photosystem membrane (see, e.g., Stirbet (1998) *Theor. Biol.* 193(1):131–51). Means to measure the redox state of a photosystem membrane of a plant are well known, e.g., using electron paramagnetic resonance (EPR) and flash photolysis (see, e.g., Hoshida (1997) Biochemistry. 36:12053–61; Gourovskaya (1997) *FEBS Lett* 414:193–6; Yruela (1996) *Biochemistry* 35:9469–74.

Selecting and Using Microorganisms

The agents and bacterial isolates of the invention can be applied as preparations purified to varying degrees, as extracts, or as secretion products of a microorganism. In one embodiment, a microorganism (which can generate a net photosynthesis-enhancing agent of the invention, either as a natural product, or because it has been recombinantly manipulated to secrete or release greater amounts of the agent) can be applied directly to the plant, e.g., the root, shoot, stem, leaf, or seed. In one embodiment, the agent or bacterial isolate, whether a microorganism, a composition derived from the microorganism, or a synthetic version of the agent, is applied to the soil or directly around or into the root of the plant or into a growth medium, as in a hydroponic controlled growth environment.

The methods of the invention include applying to a plant any microorganism, e.g., any bacterium, fungi, or yeast, capable of generating an enhancer of net photosynthesis or growth promoting agent. The bacterium, as defined above, can be, e.g., any member of the Prokaryotae (Monera) kingdom. While, without limitation, any bacteria can be used, preferred embodiments use and application of riboflavin-releasing or lumichrome-releasing *Sinorhizobium meliloti, Pseudomonas fluorescens*, and species within the genera *Rhizobium, Sinorhizobium*, or *Bradyrhizobium*. The fungi can be, e.g., any member of the Fungi kingdom. While, without limitation, any fungus can be used, preferred embodiments use and application of riboflavin-releasing or lumichrome-releasing *Glomus* (e.g., *G. mosseae* or *G. intraradices*), *Gigaspora* (e.g., *G. margarita* or *G. rosea*), *Scutellospora* (e.g., *S. castenea*) or *Aspergillus* (e.g., *A. terreus*). While, without limitation, any yeast can be used, preferred embodiments use and application of riboflavin-releasing or lumichrome-releasing *Candida*.

Soil Dwelling or Root Colonizing Microorganisms

The test compound can be applied as an isolate, an extract or a secretion product of a microorganism. In one embodiment, the microorganism can be applied directly to the plant, e.g., the root, shoot, stem, leaf. In one embodiment, the test compound, whether a microorganism or composition derived form the microorganism, is applied to the soil or directly around or into the root of the plant. Thus, microorganisms which can live in soil or can colonize roots (e.g., in root rhizospheres) are a preferred embodiment. For example, all microorganisms which are known to colonize roots are used as test compounds of the invention. The skilled artisan can further isolate root-colonizing by, e.g., isolating root nodules and rhizospheres and determining rhizobial root microorganism populations (see, e.g., Petersen (1996) *FEMS Microbiol Lett* 142:271–276; Simons (1996) *Mol. Plant Microbe Interact*. 9:600–607). See also , Kloepper, et. al., U.S. Pat. Nos. 5,503,651, and 5,503,652, describing means to isolate bacterial strains from the rhizosphere.

Exemplary bacterial species, include, e.g., *Sinorhizobium meliloti*, which invade alfalfa root nodules to establish an effective nitrogen-fixing symbiosis (see, e.g., Cheng (1998) *J. Bacteriol.* 180:5183–5191). *Pseudomonas fluorescens* are known to colonize the root tips of, e.g., alfalfa, tomato, radish, and wheat (see, e.g., Dekkers (1998) *Mol. Plant Microbe Interact*. 11:763 –771. *Agrobacterium tumefaciens* is known to infect a variety of plant roots and other cell types (see, e.g., Matthysse (1998) *Appl. Environ. Microbiol.* 64:2341–2345). *Azospirillum brasilense* and *Pseudomonas aureofaciens* are known to infect the roots (rhizospheres) of, e.g., wheat (see, e.g., Pereg-Gerk (1998) *Mol. Plant Microbe Interact*. 11:177–187; Wood (1997) *J. Bacteriol.* 179:7663–7670).

Exemplary fungal root-colonizing species include, e.g., arbuscular mycorrhizal fungi, such as *Glomus mosseae, G. intraradices, Gigaspora rosea, Scutellospora castanea* (see, e.g., Burleigh (1998) *Gene* 216:47–53; van Tuinen (1998) *Mol. Ecol.* 7:879–887). Riboflavin- or lumichrome-releasing *Candida* spp. can also be used.

Other soil dwelling microorganisms used in the methods of the invention can be readily identified by the skilled artisan. See, e.g, van Tuinen (1998) *Mol Ecol* 7:879–887, studying colonization patterns in roots by different arbuscular mycorrhizal fungi developing from a mixed community in soil; see also Di Bonito (1995) Appl. Environ. Microbiol. 61:2809–2810; Wyss (1996) Methods Mol. Biol.50:199–207. See also Naganuma (1999) *Biosci. Biotechnol. Biochem.* 63:195–198, describing methods for isolating soil yeast in the genus Lipomyces and related genera.

Preparing Net Photosynthesis-enhancing Agents and Riboflavin and Lumichrome-releasing Microorganisms Microorganisms that Generate Net Photosynthesis-enhancing Agents In one embodiment, the methods of the invention involve applying a microorganism that generates a net photosynthesis-enhancing agent of the invention, or a secretion product of that microorganism. The methods of the invention involve applying a riboflavin or lumichrome-releasing microorganism. Methodologies for culturing microorganisms, particularly in a large scale, are well known in the art, see, e.g., Moir (1990) *Bioprocess Technol* 9:67–94; Gailliot (1990) *Biotechnol Prog* 6:370–5.

In one embodiment, microorganisms which express greater than wild type levels of riboflavin or lumichrome are applied to a plant to increase growth. Cells which have been recombinantly manipulated, i.e., genetically engineered, to oversecrete are used in the methods of the invention. In a preferred embodiment, nucleic acid sequences which control riboflavin synthase are manipulated, e.g., upregulated or inserted and expressed as transduced recombinant expression systems. Such genes include, e.g., the ribC and ribD riboflavin synthase gene sequences of the invention. However, any nucleic acid sequence, e.g., coding sequence, transcriptional regulatory sequence, operon, or the like, which can be used to upregulate riboflavin or lumichrome synthesis and/or release, e.g., riboflavin synthase expression, can be used. For example, see U.S. Pat. Nos. 5,925,538 and 5,837,528, describing vectors and recombinant bacteria for overproducing riboflavin, in which nucleic acid overproducing riboflavin biosynthetic proteins is introduced in the chromosome of the host organism, e.g. at multiple sites and in multiple copies per site, using a rib operon having at least five genes. Furthermore, novel nucleic acid sequences involved in riboflavin and lumichrome synthesis are provided herein, particularly, in the sequences contained within the S. meliloti 4.248 kb fragment (SEQ ID NO:1) in plasmid pribD/C1 described herein. Means to make and select for such riboflavin or lumichrome overproducing cells are described further below.

Bacterial Extracts as Net Photosynthesis-enhancing Agents

In various embodiments, the net photosynthesis enhancing agents and bacterial extracts are isolated and purified from a microorganism or a microbial secretion. The isolation of the net photosynthesis enhancing agent or bacterial isolate can be accomplished using any methodology; for general information relating to standard purification procedures, including. e.g., selective precipitation with such substances as ammonium sulfate; electrophoresis, immunopurification, chromatography (such as HPLC, see Examples, below), and others, see, e.g., Scopes, PROTEIN PURIFCATION: PRINCIPLES AND PRACATICE, Springer-Verlag: New York (1982); Van-Bogelen (1995) *Biotechnol Annu Rev* 1:69–103; Evans (1995) *Biotechnology* 13:46–52; Perkins (1991) *J Chromatogr* 540:239–56; Sambrook Tijssen and Ausubel. See also, e.g., Afeyan, et. al., U.S. Pat. No. 5,833,861, describing chromatography methods and matrix geometry's which permit high resolution, high productivity separation of mixtures of solutes, particularly biological materials.

For example, as described below in the Examples, a net photosynthesis enhancing agent or bacterial isolate of the invention can be in the form of crude extracts of bacterial cultures. In the Examples, microbial extracts are isolated from cultured *Sinorhizobium meliloti* as fractions using column chromatography and HPLC. The fractions are subsequently demonstrated to increase net photosynthesis in an alfalfa model plant system. Fractions which were able to increase net photosynthesis, as measured increased radioactive carbon-14 in the plant, were further analyzed by as variety of techniques, including mass spectrometry, proton nuclear magnetic resonance, and UV-visible absorbance analysis.

Acetylphloroglucinols as Net Photosynthesis-enhancing Agents

The methods of the invention also use agents comprising triacetylphloroglucinol, diacetylphloroglucinol and monoacetylphloroglucinol in amounts effective for increasing net photosynthesis in a plant. These compounds were initially identified because they have general structural identity to the bacterial extract compounds D and Y of the invention (see below). Analysis of diacetylphloroglucinol, as described for compounds D (lumichrome) and Y (riboflavin), below, found that it increases net photosynthesis in plants by as much as 50% when it is applied to roots in nanomolar concentrations.

The triacetylphloroglucinol, diacetylphloroglucinol (DAPG) and monoacetylphloroglucinol agents of the invention can be generated synthetically (i.e., in vitro organic synthesis), or, can be isolated from any one of a number of bacterial which generate (and, in many cases, secrete) these compounds as natural products. For example, a number of soil bacteria, including, e.g., *Pseudomonas* species, produce diacetylphloroglucinol. See, e.g., Shanahan (1992) *J. of Chromatography* 606:171–177, describing purification of 2,4-diacetylphloroglucinol from *Pseudomonas fluorescens* by HPLC. See also, e.g., Shanahan (1993) *Analytica Chimica Acta* 272:271–277, describing a preparative chromatographic isolation method involving thin-layer and liquid chromatography to isolate monoacetylphloroglucinol and DAPG from bacteria. For description of the synthesis of triacetylphloroglucinol, see, e.g., Gulati (1943) Org. Synth. Coll. Vol II, page 522; Broadbent (1976) *Phytochemistry* 15:1785. For the synthetic generation of the triacetylphloroglucinol, DAPG and monoacetylphloroglucinol agents of the invention; see also, e.g., Campbell (1951) *J. Am. Chem. Soc.* 73:2708–2712; Cronin (1997) *FEMS Microbiol. Ecology* 23:95–106. See, e.g., Yamaki (1 994) *Phylotherapy Res.* 8:112–114, for a description of several phloroglucinols isolated from Chinese herbal drugs; and, Arisawa (1990) *Chem. Pharm. Bull.* 38:1624–1626; Bowden (1965) *J. Pharm. Pharmacol.* 17:239–242; Hisada (1972) *Yakugaku Zasshi* 92:1124–1128.

Alternatively, bacteria or other microorganisms can be recombinantly manipulated to generate (or generate more) triacetylphloroglucinol, diacetylphloroglucinol and monoacetylphloroglucinol (or any of the other net photosynthesis-enhancing agents of the invention, as described herein). For example, see, e.g., Thomashow, et al., WO 97/01572, describing DNA sequences which function specifically in the synthesis of 2,4-diacetylphloroglucinol, and bacterial strains recombinantly manipulated to secrete this compound. See also, e.g., Barea (1998) *Applied and Environmental Microbiol.* 64:2304–2307; describing an genetically engineered *Pseudomonas* strain which is an overproducer of diacetylphloroglucinol; and, Naseby (1998) *Molecular Ecology* 7:617–625; Brimecombe (1998) *Letters in Applied Microbiol.* 26:155–160; Fenton (1992) *Applied and Environmental Microbiol.* 58:3873–3878.

Lumichrome Applied as an Enhancer of Net Plant Growth

The invention provides methods for increasing plant growth by application of lumichrome to the plant in an amount effective for increasing net growth in the plant. Lumichrome, or 7, 8, dimethylalloxazine, is commonly available from commercial sources, e.g., Sigma-Aldrich, St. Louis, Mo. Lumichrome is also generated by thermal or photochemical degradation of flavin mononucleotide (FMN). Lumichrome is also generated by oxidation (including, e.g., light-catalyzed oxidation) of riboflavin; see, e.g., Fox (1998) Internat. J. Vit. Nutr. Res. 68:174–180. Lumichrome can be analyzed by a variety of methods, e.g., it fluoresces blue with a maximum around 450 nm, typical of its alloxazine ring. See also Song (1981) Analytical Biochemistry 117:32–39.

Example 3 below details the discovery that lumichrome is an enhancer of root respiration and shoot growth. Nuclear magnetic resonance, mass spectrometry and ultraviolet-visible absorption identified "compound D" (see below) as lumichrome, or 7,8,-dimethylalloxazine. Lumichrome is a breakdown product of riboflavin. Treating alfalfa roots with 3 nM lumichrome increased root respiration 21% ($P \leq 0.05$) within 48 hours. A closely linked increase in net carbon assimilation by the shoot compensated for the enhanced root respiration. Applying 5 nM lumichrome to young alfalfa roots increased plant growth by 8% ($P \leq 0.05$) after 12 days. Soaking alfalfa seeds in 5 nM lumichrome before germination increased growth by 18% ($P \leq 0.01$) over the same period. In both cases, significant growth enhancement ($P \leq 0.05$) was evident only in the shoot.

Preparing Test Compounds From Microbial Sources
Microorganisms as Test Compounds The methods of the invention involve applying a test compound comprising a microorganism from a variety of sources, as described above. Thus, the test compound can be a microorganism or a secretion product of the microorganism. Methodologies for culturing microorganisms, particularly in a large scale, are well known in the art, see, e.g., Moir (1990) *Bioprocess Technol* 9:67–94; Gailliot (1990) *Biotechnol Prog* 6:370–5.

Bacterial Extracts as Test Compounds

In one embodiment, the test compound is a bacterial extract or isolate (as defined, above) from the microorganism or the microbial secretion. The isolation of the test compound can be accomplished using any methodology; for general information relating to standard purification procedures, including. e.g., selective precipitation with such substances as ammonium sulfate; electrophoresis, immunopurification, chromatography (such as HPLC, see Examples, below), and others, see, e.g., Scopes, PROTEIN PURIFICATION: PRINCIPLES AND PRACTICE, Springer-Verlag: New York (1982); VanBogelen (1995) *Biotechnol Annu Rev* 1:69–103; Evans (1995) *Biotechnology* 13:46–52; Perkins (1991) *J Chromatogr* 540:239–56; Sambrook, MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. Greene Publishing and Wiley-Interscience, New York (1987). See also, e.g., Afeyan, et. al., U.S. Pat. No. 5,833,861, describing chromatography methods and matrix geometry's which permit high resolution, high productivity separation of mixtures of solutes, particularly biological materials.

For example, as described below, in Example 1, test compounds can be crude extracts of bacterial cultures. In the Example, microbial extracts are isolated from cultured *Sinorhizobium meliloti* as fractions using column chromatography and HPLC. The fractions are subsequently tested for their ability to increase net photosynthesis in an alfalfa model plant system. Fractions which were able to increase net photosynthesis, as measured increased radioactive carbon-14 in the plant, were further analyzed by as variety of techniques, including mass spectrometry, proton nuclear magnetic resonance, and UV-visible absorbance analysis.

Applying an Enhancer of Net Photosynthesis to a Plant

Selection of Plants

The methods of the invention and the net photosynthesis enhancing agents or bacterial isolates of the invention can be used to enhance net photosynthesis and growth in essentially any plant or seed. Thus, the methods of the invention are practiced with and incorporate use of (application to) a broad range of plants, including, e.g., species from the genera *Asparagus, Atropa, Avena, Brassica, Citrus, Citrullus, Capsicum, Cucumis, Cucurbita, Daucus, Fragaria, Glycine, Gossypium, Helianthuls, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Phaseolus, Pisum, Pyrus, Prunus, Raphanus, Secale, Senecio, Sinapis, Solanum, Sorghum, Trigonella, Triticum, Vitis, Vigna*, and *Zea*, to name just a few.

Application Methodologies

The invention involves applying a net photosynthesis enhancing agent, a bacterial isolate or medium, or a riboflavin- or lumichrome-releasing microorganism to any part of a plant, including, e.g., roots, stems, leaves, seeds and shoots. For example, if the agent is to be applied to the root, it can be in a liquid applied to soil or to a hydroponic medium (see, e.g., U.S. Pat. No. 5,918,416). The growth enhancing agents of the invention, either as chemicals or as microorganisms, can be applied to controlled growth mediums such as vermiculate-based medium, sterile or artificial soils, "solid matrix primers," and the like (see, e.g., U.S. Pat. No. 5,628,144). A seed can be soaked in a solution comprising the agent. Seeds can be inoculated with bacteria or chemicals prior to planting; such techniques are known in the art (see, e.g., U.S. Pat. No. 5,628,144). Alternatively, it can be applied as organism per se, such as a soil-dwelling or root-colonizing microbe, and subsequently generated and secreted by to microorganism. See also, e.g., U.S. Pat. No. 5,916,029, describing a process for coating seeds with dry, dormant microorganisms; U.S. Pat. No. 3,168,796; WO 92/08355.

Alternatively, the net photosynthesis enhancing agent or bacterial isolate or a riboflavin- or lumichrome-releasing microorganism can be sprayed on leaves, injected into a stalk, and the like. See also, e.g., Lloyd, et. al., U.S. Pat. No. 5,739,081, describing water dispersible granules suitable for agricultural application, where biologically active substances are loaded into preformed absorbent granules. Luthra, et. al., U.S. Pat. No. 5,652,196, describes means to apply water soluble agents to plants in a variable, controlled release manner. Behel, Jr., et. al., U.S. Pat. No. 5,632,799, describes a dried particulate, hydrophilic gel as micronutrient delivery system to plants in soil. Aoki, et. al., U.S. Pat. No. 5,676,726, describes a matrix for application as a plant culture medium which can be used as a microorganism-immobilizing support capable of delivering a large population of microorganisms with long-term viability and improved colonization and growth rates, to plants in soil.

The net photosynthesis enhancing agent or bacterial isolate and methods of the invention can also be applied to, e.g., seedlings or germinations incubated or plants grown under controlled environmental systems, such as, e.g., hydroponic systems, see, e.g., Wang (1996) *Biol Trace Elem Res* 55:147–62; http://www.usu.edu/~cp1/hydropon.html.

Riboflavin Synthesis Genes and Polypeptide

This invention provides genes and polypeptides that can induce or upregulate the expression of riboflavin synthesis genes, including riboflavin synthase, in microorganisms, particularly bacteria. The nucleic acids of the invention also include non-coding regions of these genes and complementary, or antisense, polynucleotides. As the genes and polypeptides can be expressed in vitro or in vivo, the invention provides for a variety of means of expressing these genes, including expression cassettes, vectors, cell lines, transgenic plants, and the like.

One of skill will recognize that desired phenotypes associated with altered gene activity can be obtained by modulating the expression or activity of the genes and polypeptides of the invention. Any of the known methods described for increasing or decreasing expression or protein activity can be used for this invention. The invention can be practiced in conjunction with any method or protocol known in the art, which are well described in the scientific and patent literature.

General Techniques

The nucleic acid sequences of the invention and other nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Purification of Polypeptides of the Invention

Either naturally occurring or recombinant polypeptides can be purified for use in functional assays. Naturally occurring polypeptides can be purified, e.g., from bacteria carrying polynucleotides of the invention. Recombinant polypeptides can be purified from any suitable expression system.

Polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al. supra; and Sambrook et al., supra).

A number of procedures can be employed when recombinant polypeptides are purified. For example, proteins having established molecular adhesion properties can be reversiblly fused to the polypeptides. With the appropriate ligand, polypeptides can be selectively adsorbed to a purification column and then freed from the column in a relatively pure form. The fused protein is then removed by enzymatic activity. Finally the polypeptides could be purified using immunoaffinity columns.

Riboflavin Synthesis Gene Genomic and Cis-acting Transcriptional Regulatory Sequences The present invention provides identification, characterization and isolation of genomic and ORF sequences comprising the nucleic acids of the invention, as exemplified by the genomic fragment SEQ ID NO:1 and the ORFs SEQ ID NO:2, SEQ ID NO:4, SEQ ID NO:8, SEQ ID NO:10 and SEQ ID NO:12. These sequences can be isolated by any technique, including, e.g., screening of genomic, cDNA or expression libraries by hybridization techniques, and the like. Expression libraries can be screened using antibodies generated using the exemplary polypeptides of the invention, as exemplified by SEQ ID NO:3, SEQ ID NO:5, SEQ ID NO:9, SEQ ID NO:1 and SEQ ID NO:13. Nucleic acids of the invention are identified to by within the scope of the invention by their hybridization to the exemplary nucleic acids of the invention under stringent conditions, as described above, or by sequencing and sequence identify comparisons, as described herein.

For sequence identity comparison, one sequence (i.e., an exemplary sequence of the invention, SEQ ID NO:1, SEQ ID NO:2, SEQ ID NO:4, SEQ ID NO:8, SEQ ID NO:10 and SEQ ID NO:12) acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. *Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (*see generally, Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity—and thus, whether a nucleic acid or polypeptide is within the scope of the invention, are the BLAST algorithm, such as the NCBI BLAST, the BLAST 2.0, and the BLAST-X algorithms, which are described, e.g, in Altschul et al. (1990) *J. Mol. Biol.* 215: 403–410 and Altschuel et al. (1977) *Nucleic Acids Res.* 25: 3389–3402; typically, as in the analysis described in the Examples below, these algorithms are used with the BLOSUM62 scoring matrix.

For amino acid sequences, the BLASTP program and the BLOSUM62 scoring matrix is used. Sequence similarity searches as done for the amino acid sequences of the RibC protein (SEQ ID NO:3), the ribD protein (SEQ ID NO:5), the ribBA protein (SEQ ID NO:11), the rbH protein (SEQ ID NO:13) and the glyA protein (SEQ ID NO:9) with the NCBI BLAST database tool and the BLOSUM62 scoring matrix. as described in detail below are used to identify whether a sequence has sufficient sequence identity, i.e., is substantially similar, to an exemplary nucleic acid sequence of the invention (SEQ ID NO:1, SEQ ID NO:2, SEQ ID NO:4, SEQ ID NO:8, SEQ ID NO:10 and SEQ ID NO:12) to fall within the scope of the invention.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment The BLASTN program (for nucleotide sequences) uses as defaults a wordlength (W) of 11, an expectation (E) of 10, M=5, N=4, and a comparison of both strands. For amino acid sequences, the BLASTP program uses as defaults a wordlength (W) of 3, an expectation (E) of 10, and the BLOSUM62 scoring matrix; see, e.g., Henikoff & Henikoff (1989) *Proc. Natl. Acad. Sci. USA* 89:10915. The BLAST-X parameters are described in detail in the Examples, below.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid. sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The invention further provides cis-acting transcriptional regulatory sequences, e.g., promoters and enhancers, comprising the genomic sequences of the invention, including, e.g., 5' (upstream) and 3' (downstream) of a transcriptional start site. The promoters of the invention contain cis-acting transcriptional regulatory elements involved in message expression. It will be apparent that transcriptional and translational regulatory sequences (e.g., promoter and enhancer sequences) may be readily obtained and characterized using routine molecular biological techniques. For example, additional genomic (and promoter) sequences may be obtained by screening microorganisms, e.g., bacteria, genomic libraries using nucleic acid probes comprising a sequence or subsequence as set forth in the exemplary sequences of the invention (a nucleic acid sequence is within the scope of the invention if it has the requisite sequence identity, or, if it hybridizes under stringent conditions, as defined above, to the exemplary sequences (SEQ ID NO:1, SEQ ID NO:2, SEQ ID NO:4, SEQ ID NO:8, SEQ ID NO:10 and SEQ ID NO:12) of the invention). For example, further genomic sequence can be readily identified by "chromosome walking" techniques, as described by, e.g., Hauser (1998) Plant J 16:117–125; Min (1998) Biotechniques 24:398–400. Other useful methods for further characterization of promoter sequences include those general methods described by, e.g., Pang (1997) Biotechniques 22:1046–1048; Gobinda (1993) PCR Meth. Applic. 2:318; Triglia (1988) Nucleic Acids Res. 16:8186; Lagerstrom (1991) PCR Methods Applic. 1:111; Parker (1991) Nucleic Acids Res. 19:3055. As is apparent to one of ordinary skill in the art, these techniques can also be applied to identify, characterize and isolate any genomic or cis-acting regulatory sequences corresponding to or associated with the nucleic acid and polypeptide sequences of the invention, particular those contained within the genomic fragment of SEQ ID NO:1. The riboflavin synthase promoters of the invention can be used to drive expression of the coding sequences of the invention in expression systems, or they can be inserted into microorganisms to drive increased expression of endogenous riboflavin synthase.

The riboflavin synthase genes and coding sequences of the invention can also be operably linked to any heterologous promoter, including constitutive or inducible promoters. Promoters and other transcriptional and translational regulatory elements suitable for expression in microorganisms, e.g., bacteria, yeast, fungus, are known in the art. They can include promoters derived from the microorganism in which it is desired they be expressed or they can be exogenous, e.g., as viral or synthetic promoters.

Any expression system, including expression cassette, plasmid, virus, vector and the like can be recombinantly manipulated to express riboflavin synthases in microorganisms, particular, to express the ribC or ribD riboflavin synthase coding sequences of the invention. Preparation of suitable constructs and means for introducing them into microorganisms are well known, see, e.g., Sambrook.

Manipulating Riboflavin Synthesis Gene Activity and Controlling Gene Expression

The invention provides methods comprising application to plants of microorganisms which release a greater than wild type level of riboflavin or lumichrome by increasing the activity or level of expression of riboflavin synthase in the microorganism e.g., in bacteria. Any of a number of means known in the art can be used to increase or induce riboflavin synthase expression or activity in a cell. For example, introduction of the riboflavin synthase coding sequences of the invention into a cell will generate increased amount of riboflavin or lumichrome release. While any microorganism can be targeted, such as bacteria, in a preferred embodiment, plant endophytic and soil-dwelling microorganisms are targeted.

One of skill will recognize that the polypeptides encoded by the genes of the invention, like other proteins, have different domains that perform different functions. Thus, the gene sequences need not be full length, so long as the desired functional domain of the protein is expressed in the microorganism. Modified protein chains can also be readily designed utilizing various recombinant DNA techniques well known to those skilled in the art and described in detail below. For example, the chains can vary from the naturally occurring sequence at the primary structure level by amino acid substitutions (particularly conservative substitutions, as discussed supra), additions, deletions, and the like. These modifications can be used in a number of combinations to produce the final modified protein chain.

Modification of Endogenous Riboflavin- and Lumichrome-producing Genes

The methods of the invention include application of microorganisms to plants which have been selected for or genetically engineered to release greater than wild type levels of riboflavin or lumichrome. Methods for introducing genetic mutations into microorganism genes and selecting cells with desired traits are well known. For instance, cells can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used. Cells with increase levels of riboflavin or lumichrome are selected by conventional techniques.

Alternatively, homologous recombination can be used to induce a desired phenotypic change (e.g., increased levels of riboflavin or lumichrome release) by specifically targeting the genes of the invention in vivo (see, generally, Grewal (1997) *Genetics* 146: 1221–1238; Xu (1996) *Genes Dev.* 10: 2411–2422). Homologous recombination has been demonstrated in plants (see, e.g., Puchta (1994) *Experientia* 50: 277–284; Swoboda (1994) *EMBO J.* 13: 484–489; Offringa (1993) *Proc. Natl. Acad. Sci. USA* 90: 7346–7350; Kempin (1997) *Nature* 389:802–803). For example, one means to apply homologous recombination technology to the genes of the invention involves making mutations in selected portions of a gene sequences (including 5' upstream, 3' downstream, and intragenic regions) in vitro and then introducing the modified nucleic acid into a desired cell using standard techniques.

Measuring Riboflavin Release: Selecting Overexpressing Microorganisms

The methods of the invention include use of microorganisms which express greater than wild type levels of riboflavin or lumichrome. Production of and selection for such overexpressing cells can be by, e.g., conventional selection pressure or genetic engineering, e.g., insertions of expression systems which overexpress riboflavin synthase, insertion of riboflavin synthase (e.g., ribC or ribD) transcriptional regulatory sequences, and mutagens, and the like.

Production of riboflavin can be detected and quantified by various methods. Overproduction of riboflavin is readily observed when overproducing cells are exposed to UV light at 366 nm, producing an observable, yellow fluorescence. The amount of riboflavin and lumichrome produced can be quantitated, e.g., with reverse-phase high performance liquid chromatography (HPLC) or MS, as discussed above. Cell-free supernatants from microorganisms can be fractionated over an HPLC column and monitored for riboflavin at 254 nm. By extrapolation from a standard curve, the concentration of riboflavin can be determined by the area of the peak on the chromatogram. Riboflavin can also be quantitated by fluorescence spectrophotometry. For example, samples containing riboflavin can be read in a fluorescence spectrophotometer set at an emission wavelength of 525 nm and an excitation wavelength of 450 nm. In addition, other methods known in the art are available to detect or quantitate riboflavin based on its physical and biological properties.

Riboflavin- and lumichrome-overproducing bacteria can be grown in vessels ranging from shake flasks to large "batch" fermentors, by methods known in the art. The cells (especially recombinant microorganisms) are grown under suitable growth conditions.

Increasing Net Photosynthesis in Plants by Inoculating Plants with Lumichrome-expressing Soil Bacteria Bacteria, especially soil-dwelling bacteria, expressing polynucleotides of the invention can be applied to increase net photosynthesis of plants. Bacteria that are commonly associated with a particular plant species are generally preferred to inoculate that plant species. For instance, a number of bacterial species in the Rhizobiaceae, i.e. "rhizobia", are commonly used as inoculants for agricultural legumes, including alfalfa and soybean. The benefit of these bacteria is their capacity to form a root-nodule symbiosis in which they reduce elemental $N_2$ to the ammonia that is used by the plant to synthesize amino acids.

The technology for supplying these bacteria on seeds at planting or in the furrow as a liquid or pelleted product with the seed is well-established in the commercial sector (Brockwell and Bottomley, 1995, *Soil Biol. Biochem.* 27:683–697). The benefits of supplying more competitive rhizobia, faster growing rhizobia, or simply higher numbers of rhizobia at planting are common knowledge (Weaver and Frederick, 1974, *Agronomy J.* 66:2333–236; Maier and Triplett, 1996, *Crit. Rev. Plant Sci.* 15:191–234). It is also well-established that genetic manipulation of rhizobia can increase plant yield under field conditions (Williams and Phillips, 1983, *Crop Sci.* 23:246–250; Scupham et al, 1996, *Appl. Environ. Microbiol.* 62:4260–4262).

With the teaching of this application, one of skill will recognize that bacterial inoculants expressing polynucleotides of the invention, particularly those polynucleotides that increase lumichrome availability, bacterial competitiveness in the soil, and/or nitrogen fixation, will result in viable bacteria associated with the roots of plants. Furthermore, those of skill in the art will recognize that stability of the polynucleotides of the invention in bacteria can be increased by introducing the polynucleotides into the bacterial chromosome, rather than on a plasmid. Moreover, association of such bacteria with the roots of inoculated plants leads to increase photosynthesis in the plants. Soil bacteria of particular interest include *Sinorhizobium, Bradyrhizobium* and *Rhizobium*. More particularly, *Sinorhizobium meliloti, Sinorhizobium fredii* and *Bradyrhizobium japonicum* are preferred bacterial species for expression of polynucleotides of the invention.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are provided to illustrate the present invention, and not by way of limitation.

Example 1

Identifying Novel Microbial Enhancers of Net Photosynthesis by Measuring "Delayed" Increases in Root Respiration The following example details methods for identifying novel bacteria and bacterial extracts that are net enhancers of photosynthesis by measuring their ability to increase "delayed" net root respiration in a plant.

"Delayed" increases in root respiration are typically associated with an increase in net photosynthesis. A microorganism, a bacterial isolate, or a synthetic preparation thereof, of the invention can be evaluated for efficacy or potency in a particular preparation or application by, after application to the plant, measuring a net increase in "delayed" root respiration in the plant over the measured time period (at least a three to four hour delay). Thus, measurement of "delayed" root respiration is one means to evaluate the methods and compositions of the invention.

In brief, several strains of bacteria (e.g., *Rhizobium meliloti*), dead and alive, and natural product isolates purified from *R. meliloti*, were tested for their ability to increase delayed root respiration of alfalfa (*Medicago sativa* L.) roots. Maximum respiratory increases, measured either as carbon dioxide gas ($CO_2$) evolution or as oxygen gas ($O_2$) uptake, were elicited in roots of 3-day-old seedlings by 16 hour of exposure to living or dead *R. meliloti* bacterial cells at densities of $10^7$ bacteria/mL. Excising roots after exposure to bacteria or extracts and separating them into root-tip- and root-hair-containing segments showed that respiratory increases occurred only in the root-hair region. In these assays, $CO_2$ production (generated by "delayed" increases in root respiration) by root hair plant segments increased by as much as 100% in the presence of bacteria, dead or alive.

Whole Bacteria Used as a Test Compound to Enhance Net Photosynthesis

In one embodiment of the invention, whole microorganisms, dead or alive, are applied to plants to enhance net photosynthesis and subsequent "delayed" net root respiration.

*Rhizobium meliloti* 1021 (Rm1021) (Meade (1982) J. Bacteriol. 149:114–122) were grown to the early stationary phase in a defined minimal medium (as described in Vincent (1970) In "A Manual for the Practical Study of Root-Nodule Bacteria, Blackwell Scientific Publications, Oxford, UK). Bacteria were collected by centrifugation and washed three times with sterile water before roots were inoculated. UV irradiance for killing cells in some experiments was supplied as a 25 minute treatment with a transilluminator(model T1202, Sigma). The absence of living cells in UV-killed cultures and sterile, non-inoculated control treatments was verified by plating on tryptone yeast medium.

Plant Growth

If respiration is to be measured, it is important that the plants be grown under sterile conditions for the respiration measurements (see, e.g., Guri, et al., U.S. Pat. No. 5,503,652, describing compositions and methods to prevent microbial contamination of plant tissue culture media). Seeds of alfalfa (*Medicago sativa* L. cv Moapa 69) were surface sterilized for 15 minutes in 70% ethanol, rinsed with water, and allowed to imbibe for four hours with aeration before germinating in a hydroponic system (as in Maxwell (1989) *Plant Physiol.* 91:842–847) containing nitrogen free nutrient solution (see DeJong (1981) *Plant Physiol.* 68:309–313). Each 400 mL plastic box contained one gram of seeds and produced about 400 seedlings after being maintained in a sterile manner for about three days with aeration at 25° C. under indirect sunlight supplemented with fluorescent lights. Plants used in these experiments consisted of cotyledons and roots with an occasional primary leaf.

Application of Whole Bacteria to Plants

Experiments used $5 \times 10^7$ colony-forming units (CFU) of bacteria per mL of plant nutrient solution unless otherwise noted. Bacteria were harvested from their growth medium, washed twice in sterile water, suspended in 1 mL of water and added to the plant nutrient solution of alfalfa seedlings 3 days after germination, when roots were approximately 4-cm long. Sterile water (1 mL) was added to the sterile non-inoculated controls. Plants were harvested to measure root respiration at various times, depending of the experiment. At harvest, roots were excised, blotted briefly on a paper towel, weighed, and enclosed in a 10-mL gas-tight test tube. Each replicate contained 1 gram fresh wt of roots from about 200 plants; every experiment had three or four replicates; and all experiments were repeated at least twice.

Respiration Assays

All assays were conducted for 30 minutes immediately after excision. Changes in $CO_2$, and in some experiments $O_2$, were measured at 45° C. with a thermistor detector on a Sigma 4 gas chromatograph equipped with a column (3.05 m×3.2 mm) containing Chromosorb 102 for $CO_2$ and Molecular Sieve 5A for $O_2$. Helium was used as the carrier gas at flow rates of 15 $cm^3$/min for $O_2$ and 35 $cm^3$/min for $CO_2$. The change in gas composition during the first 30 min after the roots were enclosed in the assay tubes (described above) was used to calculate respiration rates. Data were analyzed with standard statistical methods to determine SE or LSD0.05 values for comparisons of treatment effects by Student's t test or analysis of variance (see, e.g., Steel et al., (1960) Principles and Procedures of Statistics. McGraw-Hill, N.Y.).

Results: Bacterial Enhancement of Photosynthesis as Determined by "Delayed" Increases in Root Respiration Experiments in which Rm1021 bacteria were applied to roots of three day old alfalfa seedlings established that soon after four hours, root respiration began to increase significantly ($p<0.05$) relative to sterile, non-inoculated controls. At eight hours after application, the $CO_2$ production went from about 1.5 millimolar per gram (mmol/g) fresh weight per hour (wt/h) to about 2.2 mmol/g fresh wt/h, peaking at about 16 hours at 2.5 mmol/g fresh wt/h. In various experiments, the promotive effect reached a maximum about 8 to 12 hours after inoculation, and remained at high levels for at least 24 hours. $CO_2$ production by the roots was linear for more than one hour after excision. In experiments in which both $CO_2$ production and $O_2$ uptake were measured, the $CO_2$ production increased in proportion to $O_2$ uptake. Germinating seedlings in the presence of 8 mM $NH_4NO_3$ had no effect on these results. All experiments were done under N-free nutrient conditions.

Living bacteria were not required for the respiratory response because UV-killed cells also increased $CO_2$ production by the roots. In fact, dead bacteria elicited significantly higher rates of root respiration than living cells in several, but not all, experiments. For example, *R. meliloti* Rm1021 enhanced "delayed" root respiration. Roots of three day old seedlings were exposed to living or dead bacterial cells for about 20 hours. Four centimeters (cm) primary roots, including tips, were excised and analyzed, as described above. For both the dead and live Rm1021 cells after application of bacteria (for 20 hours), $CO_2$ production was about 1.0 mmol/g fresh wt/h, as compared to a sterile control at about 0.5 mmol/g fresh wt/h.

Further experiments clearly indicated that the delayed respiratory enhancement by Rm1021 occurred in the root-hair region. Bacteria were exposed to the intact plant and then roots were excised and divided into two sections, a one cm tip and a 3 cm subtending segment, which had differentiated root hairs by day three. Although root tips had a much higher rate of $CO_2$ production, Rm1021 enhanced "delayed" respiration only in the root-hair zone.

Treatments in which different numbers of Rm1021 cells were inoculated onto roots showed that at least $10^7$ colony forming units per mL (CFU/mL) were required for the maximum response. When roots of three-day-old seedlings were exposed to living or dead cells for 16 hours, root hair respiration stimulated by $10^7$ CFU/mL was at about 2.0 to 2.25 mmol/g fresh wt/h., as compared to about 1.5 mmol/g fresh wt/h. stimulated by $10^3$ to about $10^4$ CFU/mL., and about 2.0 to 1.5 mmol/g fresh wt/h. stimulated by $10^8$ CFU/mL.

The well-characterized LCOs from *Rhizobium meliloti*, which function as NOD factors (see, e.g., Spaink (1995) *Annu. Rev. Phytopathol.* 33:345–368; Savoure (1997) *Plant J.* 11:277–287), were not required for the respiratory response studied in these experiments. Mutant *Rhizobium meliloti* strain TJ1A3, which produces neither Nod-factor LCOs nor root nodules, were fully capable of eliciting increased respiration in alfalfa root segments bearing root hairs after 16 hours of exposure to intact seedlings.

Isolation of Bacterial Natural Products Enhancing Net Photosynthesis (Photosynthate Production and "Delayed" Root Respiration Based on this significant increase in delayed root respiration stimulated by living or dead bacterial cells, *R. meliloti* bacterial extracts were prepared to identify and purify some of the active (photosynthesis/photosynthate-enhancing) bacterial natural products identified using the methods of the invention.

Purification of Photosynthesis/"Delayed" Root Respiration Enhancers

Crude "compound D" (identified as lumichrome, see below) was isolated using the following procedure. Supernatant (culture medium) samples from dense *Rhizobium meliloti* 1021 bacterial cultures were collected by centrifugation and treated 4 hours with hydrophobic resin (SM-2 Bio-Beads, 30 g/L, or XAD-4, 10 g/L). Compounds adsorbing to the hydrophobic surfaces were eluted with methanol and dried under vacuum.

High pressure liquid chromatography (HPLC) analysis was next performed on the lipophilic (i.e., Bio-Bead binding) fraction isolated from these culture supernatants. Samples for HPLC were dissolved in water and injected into a HPLC system fitted with an analytical column containing reverse phase C18 resin. The column was then eluted with water at 0.5 mL/min from 0 to 10 min. From 10 to 70 minutes, a linear gradient increasing to 100% methanol was applied. The analysis continued isocratically in 100% methanol for another 20 min. Eluting compounds were monitored with a photodiode array detector. Samples collected every minute were dried by lyophilization. Under these conditions, when the bacterial cells were harvested in early stationary phase, "peak D" (crude preparation of "compound D," see below further characterization) eluted after approximately 75 minutes (no "compound Y," or riboflavin, was evident, see discussion, below).

One liter of Rm1021 cell culture filtrate yielded approximately five mg of HPLC "peak D" (purified to "compound D" as described below).

Results: Purified Bacterial Natural Products Found to Enhance Net Photosynthesis as Determined by Increases in "Delayed" Root Respiration Delayed respiration enhancement experiments showed that the partially purified compound from *R. meliloti* 1021, "peak D" (lumichrome) increased root respiration at very low, possibly picomolar, concentrations. Peak D was found to increase root respiration slowly, for 8 hours; this enhanced rate was maintained at the higher level. Specifically, very small amounts of the peak D material increased root respiration after intact seedlings had been treated for about 16 hours. Peak D material promoted respiration significantly ($P>0.05$) at $6.7\times10^{-10}$ gram per liter (g/L), where $CO_2$ production was about 1.0 mmol/g fresh wt/h. A 10-fold higher concentration produced a one-half-maximum response. The respiration enhancing effect was maximal at about $10^{-7}$ to $10^{-6}$ g/L. In these experiments, HPLC fractions were supplied to roots of three day old seedlings at the indicated concentrations; respiration was measured 16 hours later; values are means from two replicates, each containing roots of about 200 plants.

Peak D material, tested at about $10^{-6}$ g/L, required about 8 hours to elicit a maximum response, which was maintained until the end of this 20 hour experiment.

The Peak D compound differs from lipo-chitin oligosaccharides active in root nodulation because (a) it does not curl alfalfa root hairs, (b) it is synthesized by bacteria in the absence of known plant inducer molecules, and (c) it is produced by a mutant *R. meliloti* that does not synthesize known lipo-chitin oligosaccharides.

Of note is the finding that some of the partially purified bacterial preparations (identified as HPLC fractions, as discussed above) resembled known pathogenic elicitors because they produced a rapid (e.g., 15-min), transitory increase in respiration. As expected, other partially purified bacterial preparations had no activity.

Example 2

Identifying Enhancers of Net Photosynthesis by Application of Purified Bacterial Extracts The following example details the identification of novel enhancers of net photosynthesis using the alfalfa plant model by further purification of photosynthesis-enhancing extracts from *R. meliloti* 1021, as discussed above. Alfalfa roots were treated with various purified bacterial fractions, described below, and tested for their effect on net photosynthesis by measuring radioactive $^{14}CO_2$ incorporation and translocation of photosynthate to the root of the plant (which, as described above, drives an increase in "delayed" respiration).

Highly purified bacterial natural products, including the "compound D" (identified as lumichrome, see below) discussed above, and a second "compound Y" (identified as riboflavin, see below) were isolated with the following procedures: Bacterial cells were grown in 7 to 14 L lots of the standard bacterial medium for 8 to 12 days (very late stationary phase). Cells were removed by centrifugation. Hydrophobic material from the supernatant was collected on XAD-4 resin, eluted with methanol, and dried by lyophilization. The resulting pellet was solubilized in water and injected into a preparative HPLC column containing C18 resin, which had been equilibrated in water. The column was eluted at 8 mL/min using the following conditions: 0–12 minutes, water; 12–15 minutes, 30% methanol: 70% water; 15–65 minutes, 35% methanol: 65% water; and 65–112 minutes, 50% methanol: 50% water. Under these conditions, "compound Y" eluted from 55 to 62 minutes and "compound D" eluted from 106 to 112 minutes. The samples were dried by lyophilization.

Compounds D and Y were then individually purified through the following four HPLC conditions:
(a) Purification Compound D, or Lumichrome:
    Column 2: A semi-preparative HPLC column containing C18 resin was equilibrated in water, and the compound D sample, solubilized in water, was injected. The column was eluted at 2 mL/minute using the following conditions: 0–4 minutes, water; 4–64 minutes, 35% methanol: 65% water, 64–85 minutes, 40% methanol: 60% water. Under these conditions, compound D eluted from 70 to 76 minutes. The sample containing compound D was dried by lyophilization.

Column 3: A semi-preparative HPLC column containing C18 resin was equilibrated in water, and the compound D sample, solubilized in water, was injected. The column was eluted at 2 mL/minute using the following conditions: 0–6 minutes, water; 6–40 minutes, 20% acetonitrile: 80% water. Under these conditions, compound D eluted from 37 to 39 minutes. The sample containing compound D was dried by lyophilization.

Column 4: An analytical HPLC column containing a mixed-mode resin (C8/cation) was equilibrated in phosphate buffer (0.2M $K_2HPO_4$, pH 4.5), and the compound D sample, solubilized in water, was injected. The column was eluted at 0.5 mL/minute using the following conditions: 0–5 minutes, 100% phosphate buffer; 5–40 minutes, a gradient going from 0 to 35% acetonitrile with the remainder comprised of phosphate buffer, 40–50 minutes, 35% acetonitrile: 65% phosphate buffer. Under these conditions, compound D eluted from 42 to 46 minutes. The sample containing compound D was dried by lyophilization.

Column 5: To remove salt from compound D, an analytical HPLC column containing C18 resin was equilibrated in water, and the compound D sample, solubilized in water, was injected. The column was eluted at 0.5 mL/minute using the following conditions: 0–45 minutes, water, 45–55 minutes 20% acetonitrile: 80% water, 55–75 minutes, a gradient going from 20 to 40% acetonitrile with the remainder comprised of water; 75–90 minutes, a gradient going from 40 to 100% acetonitrile with the remainder comprised of water. Under these conditions, compound D eluted from 83 to 85 minutes. The sample containing compound D was dried by lyophilization. This final "column 5" product is hereinafter referred to as "purified compound D."

(b) Purification Compound Y, or Riboflavin:

Column 2: A semi-preparative HPLC column containing C18 resin was equilibrated in water, and the compound Y sample, solubilized in water, was injected. The column was eluted at 2 mL/minute using the following conditions: 0–8 minutes, water, 8–20 minutes, 20% methanol: 80% water, 20–50 minutes, 30% methanol: 70% water. Under these conditions, compound Y eluted from 41 to 49 minutes. The sample containing compound Y was dried by lyophilization.

Column 3: A semi-preparative HPLC column containing C18 resin was equilibrated in 5% acetonitrile: 95% water, and the compound Y sample, solubilized in water, was injected. The column was eluted at 2 mL/minute using the following conditions: 0–20 minutes, 5% acetonitrile: 95% water; 20–50 minutes, 8% acetonitrile: 92% water; 50–90 minutes, 10% acetonitrile: 90% water. Under these conditions, compound Y eluted from 80 to 88 minutes. The sample containing compound Y was dried by lyophilization.

Column 4: An analytical HPLC column containing a mixed-mode resin (C8/cation) was equilibrated in phosphate buffer (0.2M $K_2HPO_4$, pH 4.5), and the compound Y sample, solubilized in water, was injected. The column was eluted at 0.5 mL/minute using the following conditions: 0–5 minutes, 100% phosphate buffer; 5–40 minutes, a gradient going from 0 to 35% acetonitrile with the remainder comprised of phosphate buffer. Under these conditions, compound Y eluted from 32 to 35 minutes. The sample containing compound Y was dried by lyophilization.

Column 5: To remove salt from compound Y, an analytical HPLC column containing C18 resin was equilibrated in water, and the compound Y sample, solubilized in water, was injected. The column was eluted at 0.5 mL/minute using the following conditions: 0–45 minutes, water; 45–55 minutes 10% acetonitrile; 55–75 minutes, a gradient going from 10 to 30% acetonitrile with the remainder comprised of water; 75–90 minutes, a gradient going from 30 to 100% acetonitrile with the remainder comprised of water. Under these conditions, compound Y eluted from 82 to 84 minutes. The sample containing compound Y was dried by lyophilization. This final "column 5" product is hereinafter referred to as "purified compound Y."

Results: Purified Bacterial Natural Products Found to Enhance Net Photosynthesis Purified Compound D (Lumichrome)

Twenty hours after treating alfalfa roots with purified compound D, 25% to 30% increases in net photosynthesis was effected, as measured by radioactive $^{14}CO_2$ incorporation tests. Purified compound D was supplied at approximately 100 pM in solution surrounding roots of three day old alfalfa seedlings. Net photosynthesis was measured as radioactive $^{14}CO_2$ incorporation by exposing randomized treatments of all plants simultaneously for about 15 minutes to $^{14}CO_2$ in a single chamber with thorough mixing of the chamber atmosphere. Data points were means from two to four replicates, each of which contained approximately 400 seedlings.

The isotopic assay for measuring net photosynthesis with $^{14}CO_2$ is described in Sheikholeslam (1980) Botanical Gazette 141:48–52. Briefly, to measure net photosynthesis, intact seedling are placed in a clear plastic box with direct exposure to sunlight or artificial lights. Isotopically labeled $^{14}CO_2$ is generated in the plant chamber by injecting an acid solution through a rubber stopper in the wall of the box and into a beaker containing $^{14}C$-bicarbonate. The $^{14}CO_2$ released by that chemical reaction is distributed throughout the box with a fan. After 15 minutes of photosynthesis in the presence of $^{14}CO_2$, plants are frozen in liquid nitrogen and separated into roots, stems and leaves. The amount of $^{14}CO_2$ is measured in the various plant parts with a scintillation counter after chemical digestion of the plant matter.

Net photosynthesis, i.e., radioactive $^{14}CO_2$ incorporation, increased rapidly after application of the compound D solution at estimated concentrations of no more than 100 pM (see below), peaking after about 5 to 10 hours, depending on the experiment, at about 2.5 to 2.75 $^{14}CO_2$ cpm×$10^5$ per gram exposed alfalfa seedling cotyledon (with a negative control background of about 1.5 $^{14}CO_2$ cpm×$10^5$ per gram cotyledon); and leveling off to about 2.0 $^{14}CO_2$ cpm×$10^5$ per gram cotyledon after approximately 20 hours, the last time point of the experiment. These measurements translate into an increase in net photosynthesis as much as 45% to 75% at the 8 hour (after treating roots) time point above untreated controls before declining to the 20 hours value. At about 20 hours, the increase in net photosynthesis was about 25% to 30% over untreated control.

In another experiment, treating alfalfa seedling roots with purified compound D at a presumed concentration of about 100 pM every 48 hours for 10 days increased the final shoot dry mass (as determined by weighing) 10% relative to untreated control plants. The plants treated with compound D showed no increase in root dry weight because the photosynthate (generated by compound D-enhanced net photosynthesis) subsequently transported to the roots was used to increase dark respiration.

Purified Compound Y (Riboflavin)

Purified compound Y supplied to alfalfa roots at very low (e.g., picomolar) concentrations also increases alfalfa root respiration and, to a lesser extent, net photosynthesis. These experiments were conducted in the same manner as those described for compound D. The effect of Y on increasing root respiration in various experiments ranged from 11% to 31%, while the promotive effect on net photosynthesis was uniformly low, i.e. no more than a 7% enhancement.

Estimating Molar Concentrations of Column Fractionated Compounds D and Y

The actual active concentrations of both "purified" or "column 5" D and Y in all experiments reported here were unknown because extinction coefficients could not be calculated until weighable amounts of the purified compounds were isolated. The estimated concentrations mentioned refer to probable maximum concentrations, which were determined in the following manner When samples of bacterial medium recovered from the hydrophobic resins were run through the initial preparative HPLC column (see above), weighable amounts of crude Y and D were recovered for further purification. Using the weight of these samples in combination with the estimates of unit molecular weight determined by mass spectrometry (see below), maximum molar concentrations were estimated in various experiments. Using these procedures, rough calculations indicate that the effects of Y (i.e., "column 5-purified" riboflavin) on plants require somewhat higher concentrations than D (i.e., "column 5-purified" lumichrome), as evaluated using the experimental protocols discussed above.

Structural Analysis of HPLC Purified Compounds D and Y

Proton nuclear magnetic resonance ($^1$H-NMR) analyses of both compounds D and Y show signals consistent with two separate and distinct protons at approximately 7.75 to 8.1 PPM (see Williams, D. H. and I. Fleming. 1987. Spectroscopic Methods in Organic Chemistry. McGraw-Hill, Ltd. London). In addition, signals consistent with two aromatic methyl groups are visible at 2.45 to 2.60 PPM in both compounds D and Y. The values of the two proton signals near 8.0 indicate the protons probably are part of a heterocyclic structure. Compound D has an additional proton signal at approximately 8.5 ppm, which is consistent with a proton on an aromatic N atom. Proton NMR spectra from both compounds D and Y are consistent with the presence of several aromatic moieties linked together.

UV-visible absorbance data support these conclusions by showing multiple absorbance bands and a strong fluorescence when illuminated with UV light Compound D has absorbance maxima at 216, 260, 351, and 390 nm in methanol/water. Compound Y has absorbance maxima at 222, 266, 370, and 445 nm in methanol/water. Both compounds D and Y are degraded by light and heat (e.g., 40° C.).

Unit-resolution mass spectrometry analyses initially showed ions consistent with molecular weights of 770 and 752 atomic mass units (amu) for compounds D and Y, respectively. However, simple dilution of the compound Y sample essentially eliminated the m/z 751 ion and left m/z 375 as the dominant signal. Additional tandem MS experiments with compound Y showed once again that the m/z 375 ion produced the m/z 255 signal, which yielded n/z 212. Similarly, the compound D sample m/z 769 signal fragmented to an m/z of 261, consistent with a molecular weight of 242 amu (see discussion in Example 3).

Both compounds are moderately hydrophobic and can be removed from aqueous solution in $C_{18}$ resin. The purified compounds D and Y are soluble in both water and methanol.

Structures of Compounds D and Y Compared to Known Microbial Natural Products to Identify Additional Enhancers of Net Photosynthesis These structural analyses of compounds D and Y identify a class of organic compositions which are enhancers of net photosynthesis and plant growth. Thus, the structural characteristics of compounds D and Y were used to identify other compositions which are enhancers of net photosynthesis.

The structural characteristics of compounds D and Y were compared to the structures of known microbial, especially bacterial natural products, to identify compounds with general structural identity that also may be enhancers of net photosynthesis. A number of soil bacteria, including *Pseudomonas* species, produce a compound known as 2,4-diacetylphloroglucinol ($C_{10}H_{10}O_5$, also called 2,4-diacetyl-1,3,5-benzenetriol) and monoacetylphloroglucinol. In fact, analysis of these compounds, as described above for compounds D and Y, found that diacetylphloroglucinol increases net photosynthesis in plants by as much as 50% when it is applied to roots in nanomolar concentrations.

Synthesis of 2,4diacetylphloroglucinol has not been reported in *Rhizobium* or *Sinorhizobium* bacteria, but such activity would not be surprising because related, Gram-negative *Pseudomonas* bacteria do make this molecule. Cells grown on dextrose produce much more of both compounds D and Y than those grown on mannitol. Supplementing the culture medium with 2,4-diacetylphloroglucinol, monoacetylphloroglucinol, or phloroglucinol at final concentrations of 50 micromolar increased production of compound D by about 60% to 70%, but this procedure had no consistent effect on the production of compound Y.

Example 3

Identification of Lumichrome as an Enhancer of Root Respiration and Shoot Growth The following example further details the discovery that lumichrome is an enhancer of root respiration and shoot growth. Nuclear magnetic resonance (NMR), mass spectrometry (MS) and ultraviolet (UV)-visible absorption confirmed that *Sinorhizobium meliloti* bacteria produce lumichrome as a signal molecule that enhances root respiration in alfalfa (*Medicago sativa* L.) and triggers a compensatory increase in whole-plant net carbon assimilation.

Bacterial and Plant Growth.

*S. meliloti* 1021 was grown in 2.8-L flasks shaking at 150 rpm. The initial bacterial medium contained: major components (g/L)—$K_2HPO_4$(1.0), $KH_2PO_4$(1.0), $KNO3$(0.6), $MgSO_4$(0.13), $FeCl_3.6H_2O$(0.01), $CaCl_2.2H_2O$(0.07), mannitol (10.0) and minor components (mg/L)—thiamine (1.0), biotin (1.0), $Na_2MoO_4.2H_2O$(0.24), $H_3BO_4$(3.0), $MnSO_4.H_2O$(1.83), $ZnSO_4.7H_2O$(0.29), $CuSO_4.5H_2O$ (0.13), $CoCl_2.6H_2O$(0.12). The final, improved medium for maximum production of compound D contained: major components (g/L)—$K_2HPO_4$(1.0), $KH_2PO_4$(1.0), $KNO_3$ (6.0), proline (5.0) $MgSO_4$(0.26), $FeCl_3.6H_2O$ (0.02), $CaCl_2.2H_2O$(0.07), dextrose (10.0) and minor components (mg/L)—thiamine (2.0), biotin (2.0), $Na_2MoO_4.2H_2O$ (0.24), $H_3BO_4$(3.0), $MnSO_4.H_2O$(1.83), $ZnSO_4.7H_2O$ (0.29), $CuSO_4.5H_2O$(0.13), $CoCl_2.6H_2O$(0.24).

Moapa 69' alfalfa seeds for all experiments were soaked 30 min in 70% ethanol, rinsed with sterile water, treated 5 min in concentrated $H_2SO_4$, rinsed with sterile water, soaked 30 min in commercial bleach and then washed with sterile water. For respiration tests approximately 400 seeds (1 gram) were germinated on a 10×10-cm screen above a hydroponic nutrient solution, see Volpin (1998) Plant Physiol. 116:777–783. In some hydroponic experiments the nutrient solution was supplemented to contain ampicillin (125 mg/L) and rifampicin (10 mg/L). Plant growth experiments were done in sterile pots (10×10×10 cm) containing vermiculite. The pots were watered with the hydroponic nutrient solution (Volpin (1998) supra) supplemented to contain 1 mM $NH_4NO_3$ and various lumichrome treatments every second day. In all experiments, plants were grown under controlled conditions using a 12/12-hour day/night photoperiod and a 25/20° C. temperature regime with a photon flux density (400–700 nm) of 250 µmol/m²-s.

Compound Isolation and Identification

Supernatant from bacterial cultures was collected by centrifugation and stirred 4 hours with XAD4 resin (10 g/L). Compounds adsorbed to the resin were eluted in methanol and dried under vacuum with or without freezing. The dry pellet from 15 L of bacterial medium was solubilized in water and injected into a preparative HPLC column (Waters µBondapak $C_{18}$, 300×25 mm), which had been equilibrated in water. The column was eluted at 8 mL/min using water, 0–12 min; methanol:water (3:7), 12–15 min; methanol:water (35:65), 15–65 min; and methanol:water (1:1), 65–112 min. Under these conditions compound Y (discussed above, identified as riboflavin, below) eluted at 55 to 62 min, and compound D (discussed above, identified as lumichrome, below) eluted at 106 to 112 min. The samples were dried by lyophilization. Then compounds D and Y were individually purified through four additional HPLC separations: (1) a semi-preparative column (Alltech Hypersil $C_{18}$, 199×10 mm) was equilibrated and eluted isocratically (2 mL/min) with methanol:water (2:8) or (35:65) for compounds Y and D, respectively; (2) the same column was equilibrated and eluted isocratically (2 mL/min) with acetonitrile:water (1:9) or (2:8) for compounds Y and D, respectively; (3) an analytical column (Alltech $C_8$/cation mixed-mode, 150×4.6 mm) was equilibrated in phosphate buffer (0.2M $K_2HPO_4$, pH 4.5) and eluted at 0.5 mL/min using 100% phosphate buffer for 0–5 min; a gradient going from 0 to 35% acetonitrile with the remainder comprised of phosphate buffer for 5–40 min, and acetonitrile:phosphate buffer (35:65) for 40–50 min., under these conditions compounds Y and D eluted at 32–35 and 42–46 min, respectively; (4) finally, samples were desalted on an analytical column (Alltech Lichrosorb $C_{18}$, 250×4.6 mm) by rinsing on the column for 30 min with water and then eluting compounds Y and D with a 70-min gradient going from methanol:water (3:7) to 100% methanol.

Thin-layer chromatography (TLC) on silica-gel-coated glass (Alltech 0.2×100×100-mm 'HPTLC Silica Gel 60' plates) separated compounds in the lipophilic fraction using chloroform:methanol:water (17.5:12.5:1.5). TLC plates were viewed on a UV-light box (Sigma model T1202) and photographed with Polaroid 667 3000iso film.

UV-visible absorption spectra were recorded in methanol in a Perkin Elmer Lambda 6 dual-beam spectrophotometer. Proton nuclear magnetic resonance ($^1$H-NMR) analyses were conducted at the UCD NMR facility with a 600-MHz Bruker Avance DRX-600 operating on XWINNMR software 2.1. Tetramethylsilane was added as an internal standard to the deuterated methanol solvent. MS data were obtained at the UCD Advanced Instrumentation Facility on a Finnigan LC-ion-trap MS, model LC-Q, using negative mode electrospray ionization running at 1 mtorr He after injecting samples in methanol:water (1:1). Tandem MS experiments were conducted by increasing the translational energy of selected ions to promote collisions with He and then detecting the major daughter ions.

Biological Tests with Lumichrome

Stock solutions of 100 µM lumichrome (Sigma-Aldrich Inc., St. Louis, Mo.) were prepared in methanol:1 N HCl (49:1) by stirring for 2 hour and storing at −20° C. for 24 to 48 hours before using once and discarding. In respiration tests, lumichrome was added to the root systems of intact plants 3 or 4 days after germination. Respiration was assessed 18–40 hours later using a gas chromatograph to measure the $CO_2$ evolved by replicate samples of root segments from which meristematic tips had been removed, as described by Volpin (1998) supra. A typical replicate from 5-day-old seedlings contained 1 g fresh weight of root segments from approximately 200 plants.

Lumichrome effects on plant growth were tested by treating roots or seeds. Surface-sterilized seeds were soaked 2 hours in either 0 or 5 nM lumichrome. Then 50 seeds were planted in vermiculite in each pot. Plants germinating from untreated seeds received nutrient solution containing 0, 5 or 50 nM lumichrome. Plants developing from seeds soaked in 5 nM lumichrome were watered with lumichrome-free nutrient solution. Pots were covered initially with a clear, plastic wrap, which was removed after 6 days. Plants were harvested 12 days after germination, and roots and shoots were separated, dried, and weighed.

Optimizing Production of "Compound D"—Lumichrome

Purification and identification of compound D was facilitated by optimizing its production. First, using the initial bacterial medium (described by Volpin (1998) supra), it was established that maximum amounts of compound D were present in the supernatant of stationary-phase cultures and that extracting the bacterial cells did not increase yield of compound D markedly. Then the carbon source was modified to increase yields of the growth-enhancing agent. Replacing mannitol with maltose, lactose or dextrose at 10 g/L increased compound D production by factors of 3, 16 ($P \leq 0.01$), and 19 ($P \leq 0.001$), respectively. All subsequent work used dextrose as the carbon substrate.

When bacteria were grown on dextrose, a bright yellow compound appeared in the culture supernatant of stationary-phase cells, and it co-purified with compound D and other lipophilic components on XAD-4 resin. This material, which was termed compound Y for its yellow color, separated easily from compound D on C18 resin using methanolic gradients in HPLC analyses. When production of compounds D and Y was quantified by HPLC in cells grown at different temperatures, maximum yield of D was evident at 34° C. Thus in all subsequent work cells were grown at 34° C.

TLC analyses of 2- to 5-mL cultures of medium containing dextrose (10 g/L) further optimized production of compounds D and Y. Maximum production of compound D was observed in the dextrose medium with the following additions and modifications: proline (5.0 g/L), $KNO_3$(6.0 g/L), thiamine (2.0 mg/L), biotin (2.0 mg/L), $MgSO_4$(0.26 g/L), $FeCl_3.6H_2O$(0.02 g/L) and $CoCl_2.H_2O$(0.24 mg/L). UV-illuminated TLC plates showed compounds D and Y clearly.

Purification of Compounds D and Y

Purification of compounds D and Y was achieved by following the characteristic UV-visible absorption spectra of the molecules through nine HPLC steps. The initial preparative HPLC column separated compounds D and Y, and four additional purification steps were used for each compound before material was judged suitable for NMR and MS experiments. The blue and yellow fluorescence of compounds D and Y, respectively, facilitated the detection of trace amounts. Solubility problems with compound D in all solvents limited yields, and compound Y was only marginally better. Eventually mg quantities of compound Y and µg amounts of compound D were available for analysis.

Identification of Compounds D and Y
Nuclear Magnetic Resonance Analysis

The $^1$H-NMR spectra of compounds D and Y suggested both molecules were relatively small. The $^1$H-NMR spectra showed several minor peaks which did not change proportionally to the major proton signals in samples purified at different times. The $^1$H-NMR spectra of compounds D and Y, summarized in Table 1, indicated the molecules were structurally related. Proton-NMR analyses of compounds D and Y gave comparable signals to lumichrome and riboflavin, respectively. Data are given as $\delta_H$ (ppm) relative to tetramethylsilane for samples in deuterated methanol. Peak morphologies are represented as dd, double doublet; m, multiplet; or s, singlet. Coupling constants (J) are given in Hertz. Numbers of protons in each signal are represented as 1H or 3H. Positional assignments for riboflavin and lumichrome are shown in below:

| Assignment | Compound D | Compound Y |
|---|---|---|
| 1 | 8.08 (<1H, s) | None |
| 3 | 8.58 (1H, s) | 8.55 (<1H, s) |
| 6 | 7.75 (1H, s) | 7.97 (1H, s) |
| 7-Me | 2.54 (3H, s) | 2.59 (3H, s) |
| 8-Me | 2.52 (3H, s) | 2.49 (3H, s) |
| 9 | 7.94 (1H, s) | 7.99 (1H, s) |
| 1' | None | 5.12 (1H, m) |
| 1' | None | Not detected |
| 2' | None | 4.50 (1H, m) |
| 3' | None | 3.95 (1H, m) |
| 4' | None | 3.88 (1H, m) |
| 5' | None | 3.72 (1H, dd, J=11.6, 5) |
| 5' | None | 3.84 (1H, dd, J=11.4, 3.5) |

Mass Spectrometry (MS) Analyses

The presence of these trace impurities required that exceptional care be taken in the mass spectrometry (MS) analyses. Exploratory MS experiments tested positive and negative fast-atom-bombardment ionization, positive and negative electrospray ionization, matrix-assisted laser desorption ionization, and atmospheric pressure chemical ionization. From these MS evaluations it was determined that negative electrospray ionization measurements gave the most reproducible signals for different samples of compound Y.

The negative electrospray ionization MS analyses of compound Y repeatedly gave an unexpectedly high molecular weight, apparent [M-H] ion at m/z 751. The validity of that conclusion was supported by tandem MS experiments demonstrating that the m/z 751 ion fragmented to produce an m/z 375 signal, which broke down to yield an m/z 255 fragment. The difficulty of reconciling the simple NMR spectrum with MW=752 led us to consider a number of unsatisfactory structures. Finally, it was found that simple dilution of the compound Y sample essentially eliminated the m/z 751 ion and left m/z 375 as the dominant signal. Additional tandem MS experiments showed once again that the m/z 375 ion produced the m/z 255 signal, which yielded m/z 212.

Using the data available, a search of the Beilstein database with Beilstein CrossFire Minerva version 3.1 through http://www.library.wisc.edu:4001 indicated riboflavin was a possible candidate for compound Y. Tests with authentic riboflavin gave data that were consistent with the observed values and with the literature for $^1$H-NMR (Isobe (1988) Tet. Lett. 29:1169–1172), MS (Holzmann (1988) Org. Mass Spec. 23:789–793), and UV-visible absorbance (Yagi (1956) Methods of Biochemical Analysis 10:320–355) data. Published MS analyses (Brown (1972) Org. Mass Spec. 6:1383–1399) supported the structures of the indicated ion fragments from riboflavin.

Identification of compound D as lumichrome was facilitated by experience gained with compound Y. Initial MS analyses of compound Y were confounded by an ion at m/z 769, which fragmented in tandem MS experiments to m/z 241, and $^1$H-NMR spectra seldom gave clear signals simultaneously for both the 1-N and 3-N protons. For both purified "compound D" and lumichrome, negative electrospray ionization produced the [M-H] ion m/z 241. Tandem MS experiments fragmented the m/z 241 ion to produce the m/z 198 daughter ion. Nevertheless, direct comparisons with authentic lumichrome gave data consistent with the observed values (Table 1, above) and with the literature for $^1$H-NMR (Glebova (1977) J. Org. Chem. USSR 13:996–1001), MS (Brown (1972) supra), and UV-visible absorbance (Duren (1975) Recueil des Travaux Chimiques des Pays-Bas 94:106–109) data.

Biological Activity of Lumichrome

Biological tests confirmed that lumichrome enhanced alfalfa root respiration. Respiration of alfalfa root segments was measured after exposing intact root systems for 39 hours to S. meliloti cells ($10^7$ cfu/ml) or 3 nM lumichrome. Mean values (+SE) were reported from four replicates, each of which contained several hundred root segments. Treatment effect was significant at $P \leq 0.05$. Across several experiments, 3 to 50 nM lumichrome treatments of alfalfa roots produced significant increases in respiration ranging from 11% to 30% ($P \leq 0.05$). 21% and 27% increases in root respiration were associated with 3 nM lumichrome and S. meliloti treatments, respectively.

Tests with riboflavin showed that it too enhanced root respiration, but generally higher concentrations were required to elicit a response comparable to lumichrome. For example, in one test 200 nM riboflavin produced approximately the same increase in root respiration as 30 nM lumichrome. Such results may be the result of conversion of riboflavin to lumichrome in situ.

Longer term tests showed that, when roots were exposed to lumichrome or seeds were immersed in a lumichrome solution before germination, the treated seedlings contained significantly more dry matter than the controls. Increases ranged from 8% to 18% ($P \leq 0.05$) on a whole-plant basis, and results from several experiments showed significant increases only in shoot dry weight. For example, the root drench (5 nM and 50 nM lumichrome) and the seed soaking (5 nM lumichrome) treatments increased shoot dry weight of the plants by 7% ($P \leq 0.05$), 12% ($P \leq 0.01$), and 18% ($P \leq 0.01$), respectively, relative to the control shoots. Root masses also were numerically, but not significantly, larger in lumichrome-treated plants.

Summary

Both chemical and biological data described herein support the identification of lumichrome as a S. meliloti factor that increases alfalfa root respiration. All evidence points to lumichrome as being the active signal molecule. First, concentrations of lumichrome required for plant growth activity were lower than those of riboflavin. Second, lumichrome was detected as compound D (see discussion above) in the alfalfa rhizosphere when S. meliloti was added to the roots. Third, lumichrome is produced easily from riboflavin by both chemical and biological factors. While riboflavin has been well-established as a rhizosphere molecule, before this invention there has been no recognition that its degradation product lumichrome is ecologically relevant.

Riboflavin occurs in soil (Carpenter (1943) Science 98:109–110), presumably because many soil microorganisms including *Azospirillum* (Dahm (1993) Zentralbl. Microbiol. 148:195–203; Rodelas (1993) Plant Soil 153:97–101), *Azotobacter*(Gonzaleza-Lopez (1983) Soil Biol. Biochem. 15:711–713), *Rhizobium* (West (1938) Nature 142:397–398) and half of 63 bacterial isolates from pine roots (Strzelczyk (1980) Polish J. Soil Sci. 13:31–40) release this molecule. Some legumes, including alfalfa, also exude trace amounts of riboflavin from roots under certain conditions (Rovira (1961) Plant Soil 14:199–214). Traditional views of how bacteria benefit from the presence of riboflavin are based on the early observation that riboflavin promoted bacterial growth (West (1938) supra). The fact that riboflavin auxotrophs in rhizobia form weakly effective root nodules on legumes (Schwinghamer (1970) Aust J. Biol. Sci. 23:1187–1196) also focused past attention on riboflavin rather than lumichrome.

Riboflavin is converted to lumichrome in light by a photochemical-induced cleavage of the ribityl group under neutral and acidic conditions (Yagi (1956) supra). *Pseudomonas* bacteria enzymatically degrade riboflavin to lumichrome (Yanagita (1956) J. Biol. Chem. 221:593–607), and thus light, which may be absent in natural rhizosphere environments, is not required for production of lumichrome from riboflavin.

The primary benefit to rhizosphere bacteria of enhancing root respiration with lumichrome probably is the increased availability of $CO_2$. This conclusion certainly is supported by the proven growth requirement in rhizobia for exogenous $CO_2$ (Lowe (1962) Soil Sci. 94:351–356). Mycorrhizal fungi also grow more rapidly under elevated $CO_2$ (Becard (1989) Appl. Environ. Microbiol. 55:2320–2325) and thus could benefit from neighboring rhizobia or, possibly, from their own production of lumichrome. It is also conceivable that an increased flow of carbon substrates needed to support the additional respiration in the root cells results in enhanced exudation of plant compounds beneficial to rhizosphere bacteria Previous results showing that nanomolar amounts of riboflavin stimulated alfalfa root colonization by *S. meliloti* (Streit (1996) Molec. Plant-Microbe Interact. 9:330–338) may have reflected both direct stimulation of bacterial growth by riboflavin (West 91938) supra) and indirect stimulation through an increase in rhizosphere $CO_2$ availability. Several previous studies claimed that riboflavin stimulated plant growth (Rao (1973) Curr. Sci. 42:580–581; Gendy (1992) Beit. trop. Landw. Vet. 30:271–281), but data reported here are the first indication that lumichrome is an active factor.

Finally, these findings demonstrate that lumichrome represents a previously unrecognized mutualistic signal molecule in the *Sinorhizobium*-alfalfa association. Text book examples of Rhizobiaceae-legume interactions (Begon et al., (1990) Ecology; Blackwell Scientific Publications, Boston, $2^{nd}$ Edition) describe how the legume profits from N compounds supplied by the bacteria in the mature root nodule. Some workers have proposed that rhizobia benefit from an increase in their numbers during root colonization (Beringer (1979) Proc. R Soc. Lond. B. 204:219–233). Few workers, however, have speculated on the precise benefits to the plant which favored evolution of the intermediate stages of root nodule formation when no $N_2$ fixation is observed in modem Rhizobiaceae-legume interactions. The data reported here suggest that lumichrome produced from rhizobial riboflavin may benefit both organisms long before any $N_2$ reduction occurs. Bacteria can use the extra $CO_2$ from root respiration to grow, and plants respond to lumichrome with increases in net carbon assimilation. Therefore, lumichrome apparently functions as a mutualistic signal benefiting both the bacteria and the plant.

The production of lumichrome from riboflavin is a widely-occuring one-step process that does not limit the availabilty of lumichrome. Moreover, riboflavin synthesis is a complex, multi-step process that limits riboflavin availability and, hence, lumichrome production. Therefore, genes involved in riboflavin synthesis were isolated for expression in microorganisms, thereby increasing riboflavin production and thus lumichrome availability.

Example 4

Cloning of the ribC Gene from *Sinorhizobium meliloti* 1021

The following example details the cloning, isolation and characterization (sequencing and sequence identity comparisons) of the ribC gene from *Sinorhizobium meliloti* 1021 (SEQ ID NO:1). Also described is characterization of the RibC protein encoded by the open reading frame (ORF) of the ribC gene (amino acid sequence: SEQ ID NO;2)

Total *S. meliloti* 1021 DNA was partially digested with restriction enzyme EcoRI. 5- to 10-kb fragments were selected for ligation into cloning vector pBluescript II SK (Stratagene). *Escherichia coli* ribC mutant BSV13, which was provided by the *E. coli* Genetic Stock Center, Yale University, was used for complementation. Plasmids containing *S. meliloti* DNA were transformed into BSV 13 by electroporation. Complementary colonies were selected by spreading transformed BSV 13 on M9 minimal medium (see Sambrook, Appendix 3) containing 50 ug/ml of ampicillin and 50 ug/ml of kanamycin. Only those cells which received ribC gene can grow on this medium.

pBluescripl II SK plasmid DNA was prepared from one complementary colony and its *S. meliloti* (EcoRI) insert was isolated, characterized and sequenced. The EcoRI insert was 4248 base pairs in length.

The entire pribD/C1 *S. meliloti* (EcoRI) insert was sequenced and characterized using BLAST-X, as described in detail below. A physical map of this ribC/ribD gene complex was generated. The complementary strand— (complementary with respect to the ORFs of the four polypeptides encoded within this gene fragment, discussed below)—nucleic acid sequence of entire 4,248 base pairs of the pribD/C1 plasmid, *S. meliloti* (EcoRI) insert is SEQ ID NO:1.

Four novel *S. meliloti* genes and ORFs were thus identified: a ribC gene and ORF (residues 927 to 1547 of the ribC/ribD gene complex/pribD/C1 insert (SEQ ID NO:1)), a ribD gene and ORF (residues 1548 to 2753 of the complex/ pribD/C1 insert (SEQ ID NO:1)), an intergenic unnamed protein that is highly conserved amongst *Eubacteria* (residues 2771 to 3244 of the ribC/ribD gene complex/ pribD/C1 insert (SEQ ID NO:1)), and a serine hydroxymethyltransferase glyA gene and ORF (residues 3257 to 4237 of the ribC/ribD gene complex/pribD/C1 insert (SEQ ID NO:1)) (numbering refers to residue numbering in SEQ ID NO:1).

The open reading frame (ORF) nucleic acid sequence (SEQ ID NO:2) of the ribC gene of *Sinorhizobium meliloti* 1021 was deduced to encode a polypeptide 206 amino acids in length with the amino acid sequence displayed in SEQ ID NO:3.

Sequence similarity searches with the RibC protein amino acid sequence (SEQ ID NO:3) with the NCBI BLAST/

BLAST-X database tool used the following search parameters: Database: Non-redundant GenBank CDS; translations+PDB+SwissProt+SPupdate+PIR; Posted date: Jul. 27, 1999 3:29 PM; Number of letters in database: 122,303,564; Number of sequences in database: 399,787;

|  | K | H |
|---|---|---|
| Lambda | | |
| 0.318 | 0.135 | 0.00 |
| Gapped Lambda | | |
| 0.270 | 0.0470 | 4.94e−324 |

Matrix: BLOSUM62; Gap Penalties: Existence: 11, Extension: 1; Number of Hits to DB: 141877815; Number of Sequences: 399787; Number of extensions: 3225994; Number of successful extensions: 13314; Number of sequences better than 10.0: 194; Number of HSP's better than 10.0 without gapping: 36; Number of HSP's successfully gapped in prelim test: 61; Number of HSP's that attempted gapping in prelim test: 13043; Number of HSP's gapped (non-prelim): 244; length of query: 207; length of database: 122,303,564 effective HSP length: 53; effective length of query: 153; effective length of database: 5 101114853; effective search space: 15470572509; effective search space used: 15470572509; frameshift window, decay const: 50, 0.1; T: 12; A: 40; X1: 16 (7.3 bits) X2: 38 (14.8 bits); X3: 64 (24.9 bits); S1: 41 (21.7 bits); S2: 68 (30.9 bits).

Sequence similarity searches with the NCBI BLAST (BLAST-X) database tool indicated that the RibC protein—riboflavin synthase alpha subunit—predicated from the open reading frame was only remotely related to proteins in other bacteria:

| Protein (number of amino acids) | % Identical Residues (% sequence identity) | % Conserved Residues | Reference |
|---|---|---|---|
| RibC of *S. meliloti* 1021 (206) (SEQ ID NO:3) | 100% | 100% | This study |
| RibC of *Escherichia coli* (213) | 38 | 55 | 1 |
| RibB of *Bacillus subtilis* (215) | 35 | 53 | 2 |
| RibC of *Aquifex aeolicus* (207) | 38 | 56 | 3 |
| RibC of *Photobacterium phosphoreum* (218) | 38 | 54 | 4 |
| RibC of *Haemophilus influenzae* (204) | 35 | 56 | 5 |
| RibC of *Synechocaytis* sp (226) | 37 | 57 | 6 |
| RibC of *Photobacterium leiognathi* (218) | 35 | 53 | 7 |

References:
1. Eberhardt (1996) Eur J Biochem 242(3):712–9.
2. Schott (1990) J Biol Chem 265(8):4204–9.
3. Deckert (1998) Nature 392:353–358.
4. Lee (1994) J. Bacteriol. 176(7):2100–4.
5. Fleischmann (1995) Science 269(5223):496–512.
6. Kaneko (1996) DNA Res. 3 (3):109–136.
7. Lee (1992) Biochem Biophys Res Commun 186(2):690–697.

DNA hybridization conditions used for detecting the ribC gene and nucleic acids of the invention: an EcoRI-HindIII fragment of 408 base pairs within the ribC gene (positions 1068 to 1478 in FIG. 1) was excised and labeled with digoxigenin-11-dUTP using the random primed method (Boehringer Mannheim Biochemicals). Target DNA was transferred onto nylon membrane (MSI, MagnaGraph nylon transfer membrane). DNA hybridization was performed at 68° C. for 12 to 16 hours in 5×SSC, 1.0% blocking reagent, 0.1% N-lauroylsarcosine, 0.02% SDS. Membrane was washed twice by 2×SSC containing 0.1% SDS at room temperature for 15 minutes and twice by 0.1×SSC containing 0.1% SDS at 68° C. for 15 minutes. CDP-Star (Boehringer Mannheim Biochemicals) was used to detect labeled DNA according to manufacturer's instructions. Nucleic acids which hybridize under these "stringent" conditions to this or equivalent ribC gene probes, particularly using these wash conditions (the hybridization conditions not being the selective factor) are within the scope of the invention.

Example 5

Cloning of the ribD Gene from *Sinorhizobium meliloti* 1021

The following example details the cloning, isolation and characterization (sequencing and sequence identity comparisons) of the ribD gene (SEQ ID NO:4) and ORF from *Sinorhizobium meliloti* 1021. Also described is characterization of the amino acid sequence of the ribD protein encoded by the open reading frame (ORF) of the ribD gene (amino acid sequence: SEQ ID NO:5). The ribD gene codes for a riboflavin-specific deaminase/reductase.

The *Sinorhizobium meliloti* ribD gene was identified by complementation, isolated, sequenced, and analyzed using the same protocols as with the ribC gene, described above.

The open reading frame (ORF) of the ribD gene of *Sinorhizobium meliloti* 1021 was deduced to be 157 amino acids long with the amino acid sequence displayed in SEQ ID NO:5.

Sequence similarity searches with the amino acid sequence of the ribD protein with the NCBI BLAST database tool used the following search parameters: Database: Non-redundant GenBank CDS; translations+PDB+SwissProt+SPupdate+PIR; Posted date: Jul. 27, 1999 3:29 PM; Number of letters in database: 122,303,564; Number of sequences in database: 399,787

|  | K | H |
|---|---|---|
| Lambda | | |
| 0.317 | 0.137 | 0.00 |
| Gapped Lambda | | |
| 0.270 | 0.0470 | 4.94e−324 |

Matrix: BLOSUM62; Gap Penalties: Existence: 11, Extension: 1; Number of Hits to DB: 273796575; Number of Sequences: 399787; Number of extensions: 6578758; Number of successful extensions: 29481
Number of sequences better than 10.0: 236
Number of HSP's better than 10.0 without gapping: 41
Number of HSP's successfully gapped in prelim test: 117
Number of HSP's that attempted gapping in prelim test: 28721
Number of HSP's gapped (non-prelim): 575
length of query: 402
length of database: 122,303,564
effective HSP length: 57
effective length of query: 344 effective length of database: 99515705
effective search space: 34233402520
effective search space used: 34233402520
frameshift window, decay const: 50, 0.1
T: 12
A: 40
X1: 16 (7.3 bits)
X2: 38 (14.8 bits)
X3: 64 (24.9 bits)
S1: 41 (21.6 bits)
S2: 70 (31.7 bits)

Sequence similarity searches with the NCBI BLAST (BLAST-X) database tool indicated that the ribD protein predicated from the open reading frame was only remotely related to proteins in other bacteria:

Similarity of amino acid sequence of polypeptide encoded by *Sinorhizobium meliloti* 1021 ribD gene ORF to reported sequences in other bacteria

| Protein (number of amino acids) | % Identical residues (% sequence identity) | % Conserved residues | Reference |
|---|---|---|---|
| *Sinorhizobium meliloti* ribD (157) SEQ ID NO:5 | 100% | 100% | This study |
| *Escherichia coli* (149) | 43 | 63 | 1 |
| *Bacillus subtilis* (152) | 41 | 59 | 2 |
| *Streptomyces clavuligerus* (172) | 43 | 61 | 3 |
| *Thermotoga maritima* (156) | 48 | 66 | 4 |
| *Haemophilus influenzae* (149) | 45 | 63 | 5 |

References:
1. Taura (1992) Mol Gen Genet 234(3):429–32;
2. Lapidus (1997) Microbiology 143 (Pt 11):3431–41;
3. Kreisberg-Zakarin, R., Borovok, I., Schreiber, R., Holmgren, A., Aslund, F., Reichard, P., Unpublished;
4. Nelson (1999) Nature 399:323–329;
5. Fleischmann (1995) Science 269(5223):496–512.

Nucleic acids which hybridize under the "stringent" conditions noted above (for the ribC gene) to the ribD gene and ORF (SEQ ID NO:4), particularly using the wash conditions (washed twice by 2×SSC containing 0.1% SDS at room temperature for 15 minutes and twice by 0.1×SSC containing 0.1% SDS at 68° C. for 15 minutes), as the hybridization conditions are not the selective factor, are within the scope of the invention.

Example 6

Cloning of an Intergenic, Highly Conserved "*Eubacteria*-like" Gene From *Sinorhizobium meliloti* 1021

An intergenic, highly conserved "*Eubacteria*-like" gene from *Sinorhizobium meliloti* 1021 was isolated using the same methods as described in Example 5. The resulting gene sequence is displayed as SEQ ID NO:6. The amino acid sequence of the protein encoded by the open reading frame (ORF) of this gene is displayed as SEQ ID NO:7.

Example 7

Cloning f an Serine Hydroxymethyltransferase glyA Gene From *Sinorhizobium meliloti* 1021

The following example details the cloning, isolation and characterization (sequencing and sequence identity comparisons) of serine hydroxymethyltransferase glyA gene from *Sinorhizobium meliloti* 1021 (SEQ ID NO:8). Also described is characterization of the amino acid sequence of the protein encoded by the open reading frame(ORF) of this gene (amino acid sequence: SEQ ID NO:9). The *S. meliloti* 1021 glyA protein is 55% identical to the *E. coli* glyA.

The glyA gene codes for serine hydroxymethyltransferase, which in rhizobia probably is involved in riboflavin synthesis. There are no known reports of glyA involvement in riboflavin synthesis, but its close proximity upstream from ribD in Sm1021 and basic biochemical facts support this conclusion. For example, the hydroxymethyltransferase enzyme produced from glyA converts serine to glycine and transfers one carbon atom to tetrahydrofolate. GTP, the starting material for riboflavin synthesis requires production of the purine ring, which is made from glycine and the carbon atoms from two $N^{10}$-formyl-tetrahydrofolate molecules (Stryer, Biochemistry, 3$^{rd}$ edition. Freeman and Co., New York p. 602). The known fact that a mutation in glyA impairs root nodule formation in *Bradyrhizobium japonicum* (Rossbach and Hennecke, 1989, Molec. Microbiol. 5:39–47) permits the conclusion that riboflavin synthesis contributes to root nodule formation and $N_2$ fixation in rhizobia.

Example 8

Cloning of the ribBA Operon From *Sinorhizobium meliloti* 1021

The following example details the cloning and characterization of the *Sinorhizobium meliloti* 1021 ribBA operon.

No rib genes involved in riboflavin synthesis have been reported in rhizobia, but using procedures known to those experienced in the art (e.g. Streit et al, 1996. Molec. Plant-Microbe Interactions 9:330–338), *S. meliloti* DNA involved in riboflavin synthesis was isolated by complementing *E. coli* ribA, ribB, or ribC mutants (*E. coli* Genetic Stock Center, Yale University) with a cosmid bank of *S. meliloti* DNA in the common, Gram-negative plasmid pLAFR3 (Staskawicz et al, 1987, J. Bacteriol. 169:5789–5794). Subcloning and sequencing the one complementing cosmid with standard techniques (Streit et al, 1996. Molec. Plant-Microbe Interactions 9:330–338) showed by amino acid homology of the protein products to those of *E. coli* that in Sm1021, a putative ribD gene (59% similar) was contiguous to the ribC gene (55% similar). In addition, another gene recognized by the amino acid homology of its protein product to the *E. coli* GlyA protein (55% identical, 70% similar) was located upstream and termed glyA (Plamann MD, Stauffer GV. 1983 Gene 22(1):9–18). An additional putative open-reading frame is located between glyA and ribD. This highly conserved sequence has been reported in many bacterial species and is included here on all DNA fragments that have both glyA and ribD.

Further analysis of the *S. meliloti* DNA located an open-reading frame with high amino acid homology to the ribA and ribB genes in *E. coli* which code for a GTP cyclohydrase and a 3,4-dihydroxy-2-butanone phosphate synthase, respectively. Standard open-reading-frame analysis showed that this DNA occurs as a single gene, ribBA, in Sm1021 (SEQ ID NO:10) and is located more than 2-kb away from ribDC on the same 12-kb DNA fragment. This DNA fragment produces a bifunctional protein (SEQ ID NO:11) that complements the *E. coli* ribA and ribB mutants. Thus in *S. meliloti* the protein must serve as a bifunctional enzyme that supplies the starting materials for riboflavin synthesis from GTP and ribulose 5-phosphate.

Similarity of the ribBA open reading frame from *Sinorhizobium meliloti* 1021 to RibBA proteins (GTP cyclohydrolase II/DHBP synthase) in other bacteria is as follows:.

| Putative homologous protein (no. of amino acids) | % Identical residues | % Conserved residues | Reference |
|---|---|---|---|
| RibBA of *S. meliloti* 1021 (395) | 100 | 100 | This study |
| RibB of *Bacillus subtilis* (398) | 38 | 55 | 1 |
| RibA of *Actinobacillus pleuropneumoniae* (401) | 43 | 61 | 2 |
| RibB of *Mycobacterium tuberculosis* (425) | 42 | 62 | 3 |
| RibA of *Photbacterium leiognathi* (364) | 40 | 58 | 4 |
| RibA of *Photobacterium phosphoreum* (363) | 39 | 58 | 5 |
| RibB of *Escherichia coli* (217) | 49 | 62 | 6 |
| RibA of *Escherichia coli* (196) | 24 | 48 | 7 |
| RibB of *Haemophilus influenzae* (215) | 49 | 65 | 8 |
| RibA of *Azospirillum brasilense* (385) | 26 | 42 | 9 |

1. Sorokin A, et al. 1993 Mol Microbiol 10(2):385–95
2. Fuller T E, et al. 1995 J Bacteriol 177(24):7265–70
3. Cole S T, et al. 1998 Nature 393(6685):537–44
4. Lee C Y, et al. 1992 Biochem Biophys Res Commun 186(2):690–7
5. Lee C Y, et al. 1994 J Bacteriol 176(7):2100–4
6. Richter G, et al. 1992 J Bacteriol 174(12):4050–6
7. Richter G, et al. 1993 J Bacteriol 175(13):4045–51
8. Fleischmann R D, et al. 1995 Science 269(5223):496–512
9. Van Bastelaere et al. 1995 Gene 153(1):141–2

Example 9

Cloning of the ribH Operon From *Sinorhizobium meliloti* 1021

The following example details the cloning of ribH from *Sinorhizobium meliloti* 1021.

Uncharacterized DNA sequences available for *S. meliloti* in the Genebank database were searched for homology to *E. coli* ribH. The search resulted in the identification of the *S. meliloti* ribH homolog (35% identity to *E. coli* ribH) (Taura T, et al. 1992 Mol Gen Genet 234(3):429–32). RibH functions as the beta subunit of riboflavin synthase. This fragment was produced by PCR from Sm1021 DNA using primers selected from the nucleotide sequence in the Genebank database. The nucleotide and amino acid sequence for *S. meliloti* ribH is displayed in SEQ ID NO:12 and SEQ ID NO:13, respectively. Thus all the known genes required for riboflavin synthesis have been identified and isolated in *S. meliloti*.

Example 10

Expression of rib Genes Induces Increased Extracellular Riboflavin in *Sinorhizobium meliloi* 1021

The following example details the characterization of riboflavin production in *Sinorhizobium meliloti* 1021 expressing different rib genes.

PCR products of the three separate rib linkage groups ribBA, glyAribDC, and ribH were cloned into the broad host range vector pBBR1MCS (Kovach et al, 1994, Biotechniques 16:800–802) to test whether increasing their copy number enhances riboflavin synthesis. The PCR products were prepared with appropriate primers identified from the known *S. meliloti* sequence using a program available at htt://alces.med.umn.edu/rawprimer.html. A 35-cycle PCR reaction consisting of denaturing (30 sec, 94° C.), annealing (30 sec, 63° C.) and extension (30 sec, 72° C.) was run after an initial 3 min incubation at 94° C. The resulting products were separated by gel electrophoresis, eluted, cut with specific restriction nucleases in some cases, ligated into pBBR1MCS or pLAFR3 (Table 5), and transformed into *E. coli* cells. The pBBR1MCS and/or pLAFR3 plasmids containing the desired rib genes from *S. meliloti* were mated into Sm1021 with a classical helper plasmid technique (Figurski and Helinski, 1979, Proc. Natl. Acad. Sci., USA 76:1648–1652) used for Gram-negative bacteria to produce four recombinant strains: Sm1021 pLAFR3-ribDC, Sm1021pBBR1MCS-ribBA, Sm1021 pBBR1MCS-glyAribDC, and Sm1021pBBR1MCS-ribBA/pLAFR3-ribDC.

TABLE 5

Vectors and genes used to produce recombinant bacterial strains.

| Plasmid | Genes Inserted | Fragment Ends |
|---|---|---|
| pLAFR3 | ribDC | 402 and 3700 by PstI - From 8/99 CIP |
| pBBR1MCS | ribBA | 1 to 1418 - directly from PCR primers |
| pBBR1MCS | glyAribDC | 923 to 4915 - directly from PCR primers |

The four recombinant strains and the Sm1021 wild-type cells were grown in liquid media developed for optimum production of riboflavin (Phillips et al, 1999, Proc. Natl. Acad. Sci., USA 96:12275–12280). After 2 days, bacteria were removed and extracellular riboflavin was collected on C18 resin before being eluted and analyzed by a thin-layer chromatography technique that allows the riboflavin to be quantified under UV light (Phillips et al, 1999, Proc. Natl. Acad. Sci., USA 96:12275–12280). Representative analyses showed that pBBR1MCS-ribBA increased riboflavin production by 34 to 250%, depending on the medium, over that of Sm1021 cells (Table 6). Adding the ribDC genes enhanced riboflavin exudation somewhat (data not shown), and the combination of ribBA and ribDC increased riboflavin production 58 to 445% over wild-type cells. The nucleotide sequence containing glyAribDC increased riboflavin production by 120–365% relative to Sm1021.

TABLE 6

Effects of extra copies of rib genes on riboflavin production by *S. meliloti* 1021. Values are means ± standard error of three cultures.

| Bacteria | rib genes added | Riboflavin Production (micrograms/ml) | |
|---|---|---|---|
| | | Medium A[1] | Medium B[2] |
| Sm1021 | none | 438 ± 25 | 516 ± 20 |
| Sm1021 | pBBR1MCS-ribBA | 590 ± 59 | 1,840 ± 19 |
| Sm1021 | pBBR1MCS-ribBA/pLAFR3-ribDC | 694 ± 46 | 2,810 ± 221 |
| Sm1021 | pBBR1MCS-glyAribDC | 964 ± 96 | 2,404 ± 353 |

[1]Medium A: Major components (g/L) - $K_2HPO_4$ (1.0), $KH_2PO_4$ (1.0), $KNO_3$ (0.6), $MgSO_4$ (0.13), $FeCl_3.6H_2O$ (0.01), $CaCl_2.2H_2O$ (0.07), dextrose (10.0) and minor components (mg/L) - thiamine (1.0), biotin (1.0), $Na_2MoO_4.2H_2O$ (0.24), $H_3BO_4$ (3.0), $MnSO_4.H_2O$ (1.83), $ZnSO_4.7H_2O$ (0.29), $CuSO_4.5H_2O$ (0.13), $CoCl_2.6H_2O$ (0.12).
[2]Medium B: Major components (g/L) - $K_2HPO_4$ (1.0), $KH_2PO_4$ (1.0), $KNO_3$ (6.0), proline (5.0) $MgSO_4$ (0.26), $FeCl_3.6H_2O$ (0.02), $CaCl_2.2H_2O$ (0.07), dextrose (10.0) and minor components (mg/L) - thiamine (2.0), biotin (2.0), $Na_2MoO_4.2H_2O$ (0.24), $H_3BO_4$ (3.0), $MnSO_4.H_2O$ (1.83), $ZnSO_4.7H_2O$ (0.29), $CuSO_4.5H_2O$ (0.13), $CoCl_2.6H_2O$ (0.24).

SEQ ID NO:1

```
   1 ggaattctgg cgcacaacct ataacggccg gccgatggtc atgttcgaaa ggcggtcgag
  61 ggcatccgag gcttagagct gtatgaggaa aagtgtgtgc ggttttccgc tcgcatcccg
 121 cgtctgaact tcctggaacc gatcaccttc atgtcttaag tcgatccgac ccaaaacatg
 181 gtgatccagg ccccgcgcgg aaaagcggaa agatgaacaa ttcttaatta ttttcagcct
 241 tttacgccac cgaaacggcc acattccggt ccactttcgt gaccgttggc acggcgcgag
 301 atcctggtcg gacacaacaa ggcgcagtac caaccagtcg aaacggtcca gctttcttcg
 361 ctgcgggcga catcacccgt aaacgacccg tgctggcctg caggctgcgc tcagagaag
 421 caaacggccg tggcaggtca cgtgaccgat cgtcgctggg gcagccgcaa accaaaagg
 481 agcatgacaa tgaacagcat tgcgaaaatc tccgtcatcg ccaccctctc cgcccttacc
 541 ttcgccggaa tcttccaagc ggcgagcgtc gaaatgaact ggccggaccg gatcgaccag
 601 accgtgcgca ccttcaaggg cgacaatttc gcgttgtcg atgtcgatac gttgagccgc
 661 cagaaccaga cccgtatgcg agtagacaag gcaacaccgg ggcagcgtgc cgcattgcaa
 721 gccgctgtcg aagccaacag accgctgctc gcttcgctta gggcacgcaa tgtcgaactg
 781 gacaactgcg ccgcggcgaa gcaggcggcc gatggcggac tgacgatcta cctccgctga
 841 cctttcgggcc ggctacccga caatctcgtc cgccccccact ttcgggggcg gacttgtttt
 901 gacgggcgat ttctttcagc cagacgttat tcctgcttgg gagccgggaa ttccgccaac
 961 cgcgcggcgt agcgcgccat cgtgtccacc tcgaaattga cgagatcgcc ggacttgcgt
1021 tcgcccagg tcgtcacttc gagcgaatgt cggatcagca atacgtcgaa ttcgacgcca
1081 tccaccttgt tcacggtgag cgacgtcccg tcgagcgcca ccgagccctt gggcgcgatg
1141 aatttcgcga gatgttcggg tgccctgagg cggaagcgca cggcttcccc ctccgcttcg
1201 acggcaagga tctccgcttt gccgtcgaca tggccggaga cgatgtgacc gcccagttcg
1261 tcgccgatct tcagcgagcg ctcaagattg atgcgcgtgc cctcacgcca gtcggcgatc
1321 gtcgtcagcc tcagcgcttc ctcccatgcc tcgacctcga accagcgttc gttgctgccg
1381 gcttccggaa gtgacgtgac ggtcaggcag atgccggcat gcgcgaccga ggcacccaga
1441 tcgatcgtct gcgggtcgta attcgtggcg acgcgaagct tgatgccttc ctcgagaggt
1501 gtgaccttct cgaccgtacc gatgtcggtg atgatgcctg taaacattca gctatctctc
1561 tcgtaatcct cgaaaatatc gtcgccatag cgcgccgtgc ggcgaagcgt gaagccctcc
1621 ggcaccgacg tcctttgaaa tggggatgaa ataccacctt cgccaatggc tgccggaccg
1681 gtgaaaagca ggattcgatc caccagatcc gcatcgagaa aggaacgcgc cgctctggcc
1741 ccaccctcca cgagcaggga ggagatgccc cgggatgcaa gtgcggccag gaggtctggg
1801 atggtatcgg cgctcagcag ctcggccccc gcagcttcga gggctcctcg acgggcgtcg
1861 taatcggtcc ctgcctccgc gagcggagag aggactggtt ctcgggtcga acccgaggag
1921 agggggcaaac tgctctgccc ctcatccgcc cttcggcac ctgctccctg tcgtgggaa
1981 gaaggatagc ccgcgtctcc cgttacgacg atcagcggaa cgtcgcgcgc agtgcggacc
2041 aatttcgact cgagcggcag atcgaggcgg cggtcgagca cgatccggac cggagagcgc
2101 tcctccagcc ctggcatccg caccgtaagt tccggatcgt cggcaatggc cgtaccgata
2161 ccgacgagga tcgcgtccgt tcggcacgc aacacctgca cctgggcgcg agagacggca
2221 ccggaaatcc tcacctgccc ctcgcctctc cgtccgatca tgccgtccgc ggaaaccgca
2281 agtttcagag tcacatgcgg gcgtttcttg cgctgacgca tgaggtaggc ctcgagcaca
```

-continued

```
2341 cgcccgccct cttcatggag cgtgcctatg tcgacgtcaa tgccggcgcc gcgaagcatc 2401 accacgccgc ggccggcaac gcgttcatcg ggatcgagga tggaaacgac gacacggccg 2461 accccgagg cgatcagcgc atctgcgcag ggcgggtct tgccatgatg cgagcagggt 2521 tcgagggcga cataggcggt cgctcccctc gccttttcgc ccgcctccgc aagcgcctgc 2581 gtttccgcgt gcggtcgccc gcccggagcg gtcacggctc ggccgacgat cgtgcccttg 2641 ttgacgatga tgcagccgac cgagggattg gtggaagtca ggccgagatt gcgccttgca 2701 agccgcagcg ccgccgccat gaaacgttcg tcttcacgtg ccggctcgcc cataccgctt 2761 gttctccggg ttattcgccc ggatcgcggg caatcttggc gcttatctcg gcgatcacct 2821 tttcgaaatc ctccgcatgg gagaaatcgc gatagaccga cgcgtagcgc acgaaggcaa 2881 cgtcgtcgag gctcttcaac gcctcgagca cctgaaggcc gatttcctcc gagggaattt 2941 cggtttcgcc cgagctttcg agccggcgga cgatgcccga caccgcccgt tcgatccggt 3001 cgcgatccac cgggcgcttg cgaagcgcga tctcgaagga gcgcagcagc ttatcccggt 3061 cgaaaggaac cttccgaccg gtcttcttga tgatcatcag ctcacgcagc tgcacccgct 3121 cgaaggtcgt gaagcggccg ccgcaatccg ggcagatgcg gcggcggcga atggcgttcc 3181 cgtcctccgc cggacgggaa tccttcacct gactgtcttc ggaaccgcaa taggggcagc 3241 gcatgcagcc gtccgatcac atatagccgt acatcgggaa gcggtcggtg agcttgatca 3301 ccttctcgcg cacgccagcc tcgacagcgg cattgccctc gtcggaattg gcggccttga 3361 gaccgtcgag cacctcgacg atcagttcgc cgacctcctt gaactccgcc tccttgaagc 3421 cgcgcgtcgt accggccggt gcaccgaggc gcacgccgga ggtgacgaag gcttttcgg 3481 ggtcgaaggg aatgccgttc ttgttgcagg tgacgtagca cggccgagag cagcttcggc 3541 acgcttgcca tcgcattct tcttgcgcag gtcgaccagg catcaggtgg gtgtcggtac 3601 cgccgagacg atgtccatcc aggccgttgg ccttcaaggt ttcggcaagg gtgcgggcgt 3661 tcttgacgac ctgggccgca taatccttga aggagggctg cagcgcctcg ccaagcgcga 3721 cggccttggc ggcaatcacg tgcattagcg gcccaccctg gagaccgggg aatacggcgg 3781 agttgatctt cttggcgatt tcctcgtcat tggtgaggat catgccgccg cggggggccgc 3841 gcagggactt gtgcgtggtc gtcgtcgcaa cgtggcagtg cgggaacggc gacggatgct 3901 ggccaccggc cacgagaccg gcgatgtggg ccatgtcgac catcagccac gcgcccacct 3961 cgtcggcgat ctcgcggaag cgcttccagt cccagatgcg ggaataggcc gttccgccgg 4021 cgatgatcag tttcggcttc tgctcgcgcg ccttcctggc gacttcgtcc atgtcgagaa 4081 ggtgatcgtc ttcgcgcacg ccgtaggaaa cgacgttgaa ccatttgccc gacatgttca 4141 ccggggaccc atgggtcagg tggccgccgg aattgaggtc gaggcccatg aagtgtcgc 4201 ccggctgcag cagcgccagg aagaccgcct ggttcatctg ggagcccg
```

SEQ ID NO:2 and SEQ ID NO:3

```
1547 atgtttacaggcatcatcaccgacatcggtacggtcgagaaggtc  SEQ ID NO:2
     M  F  T  G  I  I  T  D  I  G  T  V  E  K  V   SEQ ID NO:3

1502 acacctctcgaggaaggcatcaagcttcgcgtcgccacgaattac
     T  P  L  E  E  G  I  K  L  R  V  A  T  N  Y 1457 gacccgcagacgatcgatctgggtgcctcggtcgcgcatgccggc
     D  P  Q  T  I  D  L  G  A  S  V  A  H  A  G 1412 atctgcctgaccgtcacgtcacttccggaagccggcagcaacgaa
     I  C  L  T  V  T  S  L  P  E  A  G  S  N  E 1367 cgctggttcgaggtcgaggcatgggaggaagcgctgaggctgacg
     R  W  F  E  V  E  A  W  E  E  A  L  R  L  T
```

-continued

```
1322 acgatcgccgactggcgtgagggcacgcgcatcaatcttgagcgc
      T  I  A  D  W  R  E  G  T  R  I  N  L  E  R 1277 tcgctgaagatcggcgacgaactgggcggtcacatcgtctccggc
      S  L  K  I  G  D  E  L  G  G  H  I  V  S  G 1232 catgtcgacggcaaagcggagatccttgccgtcgaagcggagggg
      H  V  D  G  K  A  E  I  L  A  V  E  A  E  G 1187 gaagccgtgcgcttccgcctcagggcacccgaacatctcgcgaaa
      E  A  V  R  F  R  L  R  A  P  E  H  L  A  K 1142 ttcatcgcgcccaagggctcggtggcgctcgacgggacgtcgctc
      F  I  A  P  K  G  S  V  A  L  D  G  T  S  L 1097 accgtgaacaaggtggatggcgtcgaattcgacgtattgctgatc
      T  V  N  K  V  D  G  V  E  F  D  V  L  L  I 1052 cgacattcgctcgaagtgacgacctggggcgaacgcaagtccggc
      R  H  S  L  E  V  T  T  W  G  E  R  K  S  G 1007 gatctcgtcaatttcgaggtggacacgatggcgcgctacgccgcg
      D  L  V  N  F  E  V  D  T  M  A  R  Y  A  A 962 cggttggcggaattcccggctcccaagcaggaataa 927
      R  L  A  E  F  P  A  P  K  Q  E  *

SEQ ID NO:4 and SEQ ID NO:5

2753 atgggcgagccggcacgtgaagacgaacgtttcatggcggcggcg  SEQ ID NO:4
      M  G  E  P  A  R  E  D  E  R  F  M  A  A  A  SEQ ID NO:5

2708 ctgcggcttgcaaggcgcaatctcggcctgacttccaccaatccc
      L  R  L  A  R  R  N  L  G  L  T  S  T  N  P 2663 tcggtcggctgcatcatcgtcaacaagggcacgatcgtcggccga
      S  V  G  C  I  I  V  N  K  G  T  I  V  G  R 2618 gccgtgaccgctccgggcgggcgaccgcacgcggaaacgcaggcg
      A  V  T  A  P  G  G  R  P  H  A  E  T  Q  A 2573 cttgcggaggcgggcgaaaaggcgaggggagcgaccgcctatgtc
      L  A  E  A  G  E  K  A  R  G  A  T  A  Y  V 2528 gccctcgaaccctgctcgcatcatggcaagacccgccctgcgca
      A  L  E  P  C  S  H  H  G  K  T  P  P  C  A 2483 gatgcgctgatcgcctcgggggtcggccgtgtcgtcgtttccatc
      D  A  L  I  A  S  G  V  G  R  V  V  V  S  I 2438 ctcgatcccgatgaacgcgttgccggccgcggcgtggtgatgctt
      L  D  P  D  E  R  V  A  G  R  G  V  V  M  L 2393 cgcggcgccggcattgacgtcgacataggcacgctccatgaagag
      R  G  A  G  I  D  V  D  I  G  T  L  H  E  E 2348 ggcgggcgtgtgctcgaggcctacctcatgcgtcagcgcaagaaa
      G  G  R  V  L  E  A  Y  L  M  R  Q  R  K  K 2303 cgcccgcatgtgactctgaaacttgcggtttccgcggacggcatg
      R  P  H  V  T  L  K  L  A  V  S  A  D  G  M 2258 atcggacggagaggcgaggggcaggtgaggatttccggtgccgtc
      I  G  R  R  G  E  G  Q  V  R  I  S  G  A  V 2213 tctcgcgcccaggtgcaggtgttgcgtgccgagacggacgcgatc
      S  R  A  Q  V  Q  V  L  R  A  E  T  D  A  I 2168 ctcgtcggtatcggtacggccattgccgacgatccggaacttacg
      L  V  G  I  G  T  A  I  A  D  D  P  E  L  T 2123 gtgcggatgccagggctggaggagcgctctccggtccggatcgtg
      V  R  M  P  G  L  E  E  R  S  P  V  R  I  V 2078 ctcgaccgccgcctcgatctgccgctcgagtcgaaattggtccgc
      L  D  R  R  L  D  L  P  L  E  S  K  L  V  R 2033 actgcgcgcgacgttccgctgatcgtcgtaacgggagacgcgggc
      T  A  R  D  V  P  L  I  V  V  T  G  D  A  G
```

-continued

```
1988 tatccttcttcccacgagcagggagcaggtgcccgaagggcggat
      Y  P  S  S  H  E  Q  G  A  G  A  R  R  A  D 1943 gaggggcagagcagtttgcccctctcctcgggttcgacccgagaa
      E  G  Q  S  S  L  P  L  S  S  G  S  T  R  E 1898 ccagtcctctctccgctcgcggaggcagggaccgattacgacgcc
      P  V  L  S  P  L  A  E  A  G  T  D  Y  D  A 1853 cgtcgaggagccctcgaagctgcgggggccgagctgctgagcgcc
      R  R  G  A  L  E  A  A  G  A  E  L  L  S  A 1808 gataccatcccagacctcctggccgcacttgcatcccggggcatc
      D  T  I  P  D  L  L  A  A  L  A  S  R  G  I 1763 tcctccctgctcgtggagggtggggccagagcggcgcgttcctttt
      S  S  L  L  V  E  G  G  A  R  A  A  R  S  F 1718 ctcgatgcggatctggtggatcgaatcctgcttttcaccggtccg
      L  D  A  D  L  V  D  R  I  L  L  F  T  G  P 1673 gcagccattggcgaaggtggtatttcatccccatttcaaaggacg
      A  A  I  G  E  G  G  I  S  S  P  F  Q  R  T 1628 tcggtgccggagggcttcacgcttcgccgcacggcgcgctatggc
      S  V  P  E  G  F  T  L  R  R  T  A  R  Y  G 1583 gacgatattttcgaggattacgagagagatagctga 1548
      D  D  I  F  E  D  Y  E  R  D  S  *

SEQ ID NO:6 and SEQ ID NO:7

3244 atgcgctgcccctattgcggttccgaagacagtcaggtgaaggat SEQ ID NO:6
      M  R  C  P  Y  C  G  S  E  D  S  Q  V  K  D  SEQ ID NO:7

3199 tcccgtccggcggaggacgggaacgccattcgccgccgccgcatc
      S  R  P  A  E  D  G  N  A  I  R  R  R  R  I 3154 tgcccggattgcggcggccgcttcacgaccttcgagcgggtgcag
      C  P  D  C  G  G  R  F  T  T  F  E  R  V  Q 3109 ctgcgtgagctgatgatcatcaagaagaccggtcggaaggttcct
      L  R  E  L  M  I  I  K  K  T  G  R  K  V  P 3064 ttcgaccgggataagctgctgcgctccttcgagatcgcgcttcgc
      F  D  R  D  K  L  L  R  S  F  E  I  A  L  R 3019 aagcgcccggtggatcgcgaccggatcgaacgggcggtgtcgggc
      K  R  P  V  D  R  D  R  I  E  R  A  V  S  G 2974 atcgtccgccggctcgaaagctcgggcgaaaccgaaattccctcg
      I  V  R  R  L  E  S  S  G  E  T  E  I  P  S 2929 gaggaaatcggccttcaggtgctcgaggcgttgaagagcctcgac
      E  E  I  G  L  Q  V  L  E  A  L  K  S  L  D 2884 gacgttgccttcgtgcgctacgcgtcggtctatcgcgatttctcc
      D  V  A  F  V  R  Y  A  S  V  Y  R  D  F  S 2839 catgcggaggatttcgaaaaggtgatcgccgagataagcgccaag
      H  A  E  D  F  E  K  V  I  A  E  I  S  A  K 2794 attgcccgcgatccgggcgaataa 2771
      I  A  R  D  P  G  E  *

SEQ ID NO:8 and SEQ ID NO:9

4555 atgctttcacagaccaacgacgctttcttcacccgctctctcgcc SEQ ID NO:8
      M  L  S  Q  T  N  D  A  F  F  T  R  S  L  A  SEQ ID NO:9

4510 gacagcgatccggaaatcttcggtgcgatcgagaaggagctgggc
      D  S  D  P  E  I  F  G  A  I  E  K  E  L  G 4465 cgccagcgccatgagatcgagctgatcgcctccgagaacatcgtt
      R  Q  R  H  E  I  E  L  I  A  S  E  N  I  V 4420 tcacgggccgtgctcgaggcgcagggctcgatcatgaccaacaaa
      S  R  A  V  L  E  A  Q  G  S  I  M  T  N  K
```

-continued

```
4375 tacgccgagggttaccggtgcaagcgctattacggcggctgccaa
     Y  A  E  G  Y  P  G  K  R  Y  Y  G  G  C  Q 4330 tatgtcgatatcgccgaggcactcgcgatcgagcgcgccaagaag
     Y  V  D  I  A  E  A  L  A  I  E  R  A  K  K 4285 ctcttcggcgtcaacttcgcgaacgtgcaaccgaattcgggctcc
     L  F  G  V  N  F  A  N  V  Q  P  N  S  G  S 4240 cagatgaaccaggcggtcttcctggcgctgctgcagccgggcgac
     Q  M  N  Q  A  V  F  L  A  L  L  Q  P  G  D 4195 accttcatgggcctcgacctcaattccggcggccacctgacccat
     T  F  M  G  L  D  L  N  S  G  G  H  L  T  H 4150 gggtccccggtgaacatgtcgggcaaatggttcaacgtcgtttcc
     G  S  P  V  N  M  S  G  K  W  F  N  V  V  S 4105 tacggcgtgcgcgaagacgatcaccttctcgacatggacgaagtc
     Y  G  V  R  E  D  D  H  L  L  D  M  D  E  V 4060 gccaggaaggcgcgcgagcagaagccgaaactgatcatcgccggc
     A  R  K  A  R  E  Q  K  P  K  L  I  I  A  G 4015 ggaacggcctattcccgcatctgggactggaagcgcttccgcgag
     G  T  A  Y  S  R  I  W  D  W  K  R  F  R  E 3970 atcgccgacgaggtgggcgcgtggctgatggtcgacatggcccac
     I  A  D  E  V  G  A  W  L  M  V  D  M  A  H 3925 atcgccggtctcgtggccggtggccagcatccgtcgccgttcccg
     I  A  G  L  V  A  G  G  Q  H  P  S  P  F  P 3880 cactgccacgttgcgacgacgaccacgcacaagtccctgcgcggc
     H  C  H  V  A  T  T  T  T  H  K  S  L  R  G 3835 ccccgcggcggcatgatcctcaccaatgacgaggaaatcgccaag
     P  R  G  G  M  I  L  T  N  D  E  E  I  A  K 3790 aagatcaactccgccgtattccccggtctccagggtgggccgctg
     K  I  N  S  A  V  F  P  G  L  Q  G  G  P  L 3745 atgcacgtgattgccgccaaggccgtcgcgcttggcgaggcgctg
     M  H  V  I  A  A  K  A  V  A  L  G  E  A  L 3700 cagccctccttcaaggattatgcggcccaggtcgtcaagaacgcc
     Q  P  S  F  K  D  Y  A  A  Q  V  V  K  N  A 3655 cgcacccttgccgaaaccttgaaggccaacggcctggatggacat
     R  T  L  A  E  T  L  K  A  N  G  L  D  G  H 3610 cgtctcggcggtaccgacacccacctgatgcctggtcgacctgcg
     R  L  G  G  T  D  T  H  L  M  P  G  R  P  A 3565 caagaagaatgcgaccggcaagcgtgccgaagctgctctcggccg
     Q  E  E  C  D  R  Q  A  C  R  S  C  S  R  P 3520 tgctacgtcacctgcaacaagaacggcattcccttcgaccccgaa
     C  Y  V  T  C  N  K  N  G  I  P  P  D  P  E 3475 aagcccttcgtcacctccggcgtgcgcctcggtgcaccggccggt
     K  P  F  V  T  S  G  V  R  L  G  A  P  A  G 3430 acgacgcgcggcttcaaggaggcggagttcaaggaggtcggcgaa
     T  T  R  G  F  K  E  A  E  F  K  E  V  G  E 3385 ctgatcgtcgaggtgctcgacggtctcaaggccgccaattccgac
     L  I  V  E  V  L  D  G  L  K  A  A  N  S  D 3340 gagggcaatgccgctgtcgaggctggcgtgcgcgagaaggtgatc
     E  G  N  A  A  V  E  A  G  V  R  E  K  V  I 3295 aagctcaccgaccgcttcccgatgtacggctatatgtga 3257
     K  L  T  D  R  F  P  M  Y  G  Y  M  *

SEQ ID NO:10 and SEQ ID NO:11

106 atgtcctacgaccagaagcgcgtcgtcgaagccattcgcgccttc  SEQ ID NO:10
     M  S  Y  D  Q  K  R  V  V  E  A  I  R  A  F   SEQ ID NO:11
```

-continued

```
151 gaagcaggcgagatcgtcgtcgtcaccgacgacggcggccgtgag
    E  A  G  E  I  V  V  V  T  D  D  G  G  R  E 196 aacgagggcgacctgatcgtcgcagcggtgcactgcacgcctgag
    N  E  G  D  L  I  V  A  A  V  H  C  T  P  E 241 aagatggcgttcatcgtgcgccatacctccggcatcgtctgcacg
    K  M  A  F  I  V  R  H  T  S  G  I  V  C  T 286 ccgatgccgcgcgaggaggcaaaacgcctcaacctgaatgcgatg
    P  M  P  R  E  E  A  K  R  L  N  L  N  A  M 331 gttgccgagaacgactccgcccacaccaccgccttcacggtgtcg
    V  A  E  N  D  S  A  H  T  T  A  F  T  V  S 376 gtcgatttcaagcacgggaccacgaccggcatttccgcagacgac
    V  D  F  K  H  G  T  T  T  G  I  S  A  D  D 421 cgaacgcttacggtcagaaaccttgccaatccgaatgtcgggccg
    R  T  L  T  V  R  N  L  A  N  P  N  V  G  P 466 acggatttcgtccggccgggccacatattccctctcgtggcgcgc
    T  D  F  V  R  P  G  H  I  P  P  L  V  A  R 511 gagggcggcgtgctgatgcgctccggccataccgaggccgccgtc
    E  G  G  V  L  M  R  S  G  H  T  E  A  A  V 556 gatctctgcaggctcgcgagcctgccgccgatcggcgtcatctgc
    D  L  C  R  L  A  S  L  P  P  I  G  V  I  C 601 gaactcgtcaacgatgacggcaccgtcatgcgtgggccgcaggtc
    E  L  V  N  D  D  G  T  V  M  R  G  P  Q  V 646 gaagccttcgcggaaacgcacggcctgaagcaggtctccgtggcc
    E  A  F  A  E  T  H  G  L  K  Q  V  S  V  A 691 gatctcattgcctatcgccagcgcaaggagaccttgatcgagcag
    D  L  I  A  Y  R  Q  R  K  E  T  L  I  E  Q 736 ggccattccttcgaaatggacacgccctacggcaaggccaagggc
    G  H  S  F  E  M  D  T  P  Y  G  K  A  K  G 781 cacacctattcgctgccctgggatacgatgcagcacctggccgtg
    H  T  Y  S  L  P  W  D  T  M  Q  H  L  A  V 826 gttttcggagacattcgcgacggcgtcgacattcccgtgcgtctc
    V  F  G  D  I  R  D  G  V  D  I  P  V  R  L 871 cacctcgaaaatgtcggagccgacgtcttcggccgcggccgccag
    H  L  E  N  V  G  A  D  V  F  G  R  G  R  Q 916 atcgacgagatcatgaagcgcatcgccgccgaggggaggggcgtc
    I  D  E  I  M  K  R  I  A  A  E  G  R  G  V 961 atcgtctatctgcgggagggctccgtgggggtcggaatttcgcag
    I  V  Y  L  R  E  G  S  V  G  V  G  I  S  Q 1006 acagcgcgaaagggcaagcacgagagggaggtccactcggaggca
     T  A  R  K  G  K  H  E  R  E  V  H  S  E  A 1051 caggagcgcgaaagcgagtggctggagatcggcctcggcgcgcac
     Q  E  R  E  S  E  W  L  E  I  G  L  G  A  H 1096 atcctgaaagacctcggcatcacctccattcgccttctttcgtcg
     I  L  K  D  L  G  I  T  S  I  R  L  L  S  S 1141 cgcgagcggcattatgtcggcctggagggcttcggcatcaagatc
     R  E  R  H  Y  V  G  L  E  G  F  G  I  K  I 1186 gccgctaccgagattctgtcaatccggaagagcccaaaatcaaag
     A  A  T  E  I  L  S  I  R  K  S  P  K  S  K 1231 ccgcgtcacccgacgcggctccctcgccttgaagcaagctgccgt
     P  R  H  P  T  R  L  P  R  L  E  A  S  C  R 1276 tacggcagggcgtcgtag 1293
     Y  G  R  A  S  *
```

SEQ ID NO:12 and SEQ ID NO:13

```
                                                       -continued
379 atggcgaagatcaagcccgtccacatcctgattgtggaagcgcgt  SEQ ID NO:12
    M   A   K   I   K   P   V   H   I   L   I   V   E   A   R     SEQ ID NO:13

424 ttctatgacgatatggccgacgcgatgctcgatggagcgaaacat
    P   Y   D   D   M   A   D   A   M   L   D   G   A   K   H 469 gcgctggatgcggccggcgccacttatatattgtgcggtcccggg
    A   L   D   A   A   G   A   T   Y   I   L   C   G   P   G 514 gcactggaaattcccgcggcgatcgccatggcgctcgatggtgcc
    A   L   E   I   P   A   A   I   A   M   A   L   D   G   A 559 gacgaaggcggggcggaatatgacggcttcgttgcgctcggcatg
    D   E   G   G   A   E   Y   D   G   F   V   A   L   G   M 604 gtgatccgcggcgagacctaccatttcgacatcgtcgccaacgag
    V   I   R   G   E   T   Y   H   F   D   I   V   A   N   E 649 tccgcgcgcgcgctgatggatctcgccgtcagcgagagcctggcg
    S   A   R   A   L   M   D   L   A   V   S   E   S   L   A 694 ctcggcaacggcattctgacggtcgagaacgacgagcaggcctgg
    L   G   N   G   I   L   T   V   E   N   D   E   Q   A   W 739 gcacgggcccgccgtacggaaggcgacaagggcggattcgccgcg
    A   R   A   R   R   T   E   G   D   K   G   G   F   A   A 784 cgcgccgccctgaccatgatcgaactgaagcaaagattgggcgca
    R   A   A   L   T   M   I   E   L   K   Q   R   L   G   A 829 gagaagtga 837
    E   K   *

SEQ ID NO:14
ribCF
5'-GACGTTATTCCTGCTTGGGAG-3'

SEQ ID NO:15
ribCR
5'-GATATTTTCGAGGATTACGAGAG-3'

SEQ ID NO:16
ribDF
5'-AAACATTCAGCTATCTCTCTCGT-3'

SEQ ID NO:17
ribDR
5'-TCTATCGCGATTTCTCCCATG-3'

SEQ ID NO:18
glyAF
5'-CAGCCGTCCGATCACATATAG-3'

SEQ ID NO:19
glyAR
5'-AGTAGACCGGGACCTCTTCGG-3'

SEQ ID NO:20
ribBAF
5'-GGCGGCTGAAGTAACTCCACT-3'

SEQ ID NO:21
ribBAR
5'-AAGACGAGCTTCTCAAGACCT-3'

SEQ ID NO:22
ribHF
5'-ATGCCGATATCCTTGAGACCG-3'

SEQ ID NO:23
ribHR
5'-GTCTGCCCGGAGATAGGTGTC-3'
```

What is claimed is:

1. A method for increasing net growth in a plant or seed, the method comprising applying an agent to the plant or seed in an amount effective for increasing net growth in the plant, wherein the agent comprises isolated lumichrome.

2. The method of claim 1, comprising applying the agent to a root, a shoot, a leaf, or a seed of the plant.

3. The method of claim 1, wherein said agent has a lumichrome concentration of about 3 nM to about 50 nM.

4. The method of claim 1, comprising applying said agent to said plant in multiple applications.

5. The method of claim 4, comprising applying to said agent to said plant about every 24 to 48 hours.

6. The method of claim 1, wherein said plant is an angiosperm.

7. The method of claim 6, wherein said angiosperm selected from the group consisting of monocotyledonous plants and dicotyledonous plants.

8. The method of claim 7, wherein said dicotyledonous plant is a legume.

9. The method of claim 8, wherein said legume is alfalfa.

* * * * *